US009783783B2

(12) United States Patent
Zhou

(10) Patent No.: US 9,783,783 B2
(45) Date of Patent: Oct. 10, 2017

(54) COMPOSITIONS AND METHODS FOR THE EXPANSION OF STEM CELLS

(71) Applicant: CORNELL UNIVERSITY, Ithaca, NY (US)

(72) Inventor: Pengbo Zhou, Princeton Junction, NJ (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/764,346

(22) PCT Filed: Jan. 29, 2014

(86) PCT No.: PCT/US2014/013509
§ 371 (c)(1),
(2) Date: Jul. 29, 2015

(87) PCT Pub. No.: WO2014/120714
PCT Pub. Date: Aug. 7, 2014

(65) Prior Publication Data
US 2015/0368613 A1 Dec. 24, 2015

Related U.S. Application Data

(60) Provisional application No. 61/758,541, filed on Jan. 30, 2013.

(51) Int. Cl.
C07K 14/47 (2006.01)
C12N 5/0789 (2010.01)
A61K 35/28 (2015.01)

(52) U.S. Cl.
CPC ............ *C12N 5/0647* (2013.01); *A61K 35/28* (2013.01); *C07K 14/47* (2013.01); *C07K 14/4702* (2013.01); *C12N 2501/125* (2013.01); *C12N 2501/145* (2013.01); *C12N 2501/26* (2013.01); *C12N 2501/60* (2013.01)

(58) Field of Classification Search
CPC .. C07K 14/4702; C07K 14/47; C12N 5/0647; A61K 35/28
See application file for complete search history.

(56) References Cited

U.S. PATENT DOCUMENTS

| | | | |
|---|---|---|---|
| 5,716,827 A | 2/1998 | Tsukamoto et al. | |
| 5,759,793 A | 6/1998 | Schwartz et al. | |
| 6,072,048 A | 6/2000 | Riley | |
| 6,399,764 B1 | 6/2002 | Riley | |
| 7,994,114 B2 | 8/2011 | Merzouk et al. | |
| 8,017,393 B2 | 9/2011 | Lanza et al. | |
| 8,039,436 B2 | 10/2011 | Sauvageau et al. | |
| 2008/0300187 A1 | 12/2008 | Sauvageau et al. | |
| 2009/0191171 A1 | 7/2009 | Ma | |

FOREIGN PATENT DOCUMENTS

WO WO 2010/042800 A1 4/2010
WO WO 2014/113415 A1 7/2014

OTHER PUBLICATIONS

International Search Report dated May 22, 2014 received from International Application No. PCT/US2014/013509.
Amsellem S. et al., "Ex Vivo Expansion of Human Hematopoietic Stem Cells by Direct Delivery of the HOXB4 Homeoprotein", Nature Medicine 9(11):1423-1427 (Nov. 2003).
Ando K. et al., "Direct Evidence for Ex Vivo Expansion of Human Hematopoietic Stem Cells", Blood 107 (8):3371-3377 (Apr. 15, 2006).
Antonchuk J. et al., "HOXB4-Induced Expansion of Adult Hematopoietic Stem Cells Ex Vivo", Cell 109:39-45 (Apr. 5, 2002).
Auvray C. et al., "HOXC4 Homeoprotein Efficiently Expands Human Hematopoietic Stem Cells and Triggers Similar Molecular Alterations as HOXB4", Haematologica 97(2):168-178 (2012).
Caré A. et al., "Enforced Expression of HOXB7 Promotes Hamatopoietic Stem Cell Proliferation and Myeloid-Restricted Progenitor Differentiation", Oncogene 18:1993-2001 (1999).
Ch'Ng J.L.C. et al., "Antisense RNA Complementary to 3' Coding and Noncoding Sequences of Creatine Kinase is a Potent Inhibitor of Translation in Vivo", Proc. Natl. Acad. Sci. USA 86:10006-10010 (Dec. 1989).
Dahlberg A. et al., "Ex Vivo Expansion of Human Hematopoietic Stem and Progenitor Cells", Blood 117 (23):6083-6090 (Jun. 9, 2011).
Huang C-H et al., "Purified Recombinant TAT-Homeobox B4 Expands CD34+ Umbilicol Cord Blood and Peripheral Blood Progenitor Cells Ex Vivo", Tissue Engineering: Part C 16(3):487-496 (Nov. 3, 2010).
Kaufman D.S., "Toward Clinical Therapies Using Hematopoietic Cells Derived from Human Pluripotent Stem Cells", Blood 114(17):3513-3523 (Oct. 22, 2009).
Kroon E. et al., "HOXA9 Transform Primary Bone Marrow Cells Through Specific Collaboration with Meis1a But Not Pbx1b", The EMBO Journal 17(13):3714-3725 (1998).
Krosl J. et al., "In Vitro Expansion of Hematopoietic Stem Cells by Recombinant TAT-HOXB4 Protein", Nature Medicine 9(11):1428-1432 (Nov. 2003).
Liu L. et al., "Essential Role of the CUL4B Ubiquitin Ligase in Extra-Embryonic Tissue Development During Mouse Embryonic Tissue Development During Mouse Embryogenesis", Cell Research 22:1258-1269 (2012).
Lu S-J et al., "Recombinant HoxB4 Fusion Proteins Enhance Hematopoietic Differentiation of Human Embryonic Stem Cells", Stem Cells and Development 16:547-559 (2007).
Pereira C-F et al., "Induction of a Hemogenic Program in Mouse Fibroblasts", Cell Stem Cell 13:205-218 (Aug. 1, 2013).

(Continued)

Primary Examiner — Daniel C Gamett
(74) Attorney, Agent, or Firm — Scully, Scott, Murphy & Presser, P.C.

(57) ABSTRACT

The present disclosure relates to methods for expansion of stem cell populations using a polypeptide that enhances stem cell growth and proliferation. The present disclosure further relates to novel homeobox protein mutants (e.g., HOXA9 and HOXB4 mutant proteins) and the use thereof to expand certain stem cell populations. The present disclosure also provides methods for treating a subject in need of transplantation of stem cells.

27 Claims, 17 Drawing Sheets

(56) References Cited

OTHER PUBLICATIONS

Sauvageau G. et al., "Overexpression of HOXB4 in Hematopoietic Cells Causes the Selective Expansion of More Primitive Populations in Vitro and in Vivo", Genes & Development 9:1753-1765 (1995).

Sauvageau G. et al., "Differential Expression of Homeobox Genes in Functionally Distinct CD34+ Subpopulations of Human Bone Marrow Cells", Proc. Natl. Acad. Sci. USA 91:12223-12227 (Dec. 1994).

Scharfmann R. et al., "Long-Term in Vivo Expression of Retrovirus-Mediated Gene Transfer in Mouse Fibroblast Implants", Proc. Natl. Acad. Sci. USA 88:4626-4630 (Jun. 1991).

Tang Y. et al., "Expansion of Hematopoietic Stem Cells from Normal Donors and Bone Marrow Failure Patients by Recombinant HOXB4", Br. J. Haematol. 144(4):603-612 (Feb. 2009).

Thorsteinsdottir U. et al., "Enhanced in Vivo Regenerative Potential of HOXB4-Transduced Hematopoietic Stem Cells With Regulation of Their Pool Size", Blood 94(8):2605-2612 (Oct. 15, 1999).

Wang C. et al., "TGFβ Inhibition Enhances the Generation of Hematopoietic Progenitors from Human ES Cell-Derived Hemogenic Endothelial Cells Using a Stepwise Strategy", Cell Research 22:194-207 (2012).

Zhang Y. et al., "CUL-4A Stimulates Ubiquitylation and Degradation of the HOXA9 Homeodomain Protein", The EMBO Journal 22(22):6057-6067 (2003).

Zhang X-B et al., "High Incidence of Leukemia in Large Animals After Stem Cell Gene Therapy With a HOXB4-Expression Retroviral Vector", The Journal of Clinical Investigation 118(4):1502-1510 (Apr. 2008).

Kirito, K., "Thrombopoietin stimulates Hoxb4 expression: an explanation for the favorable effects of TPO on hematopoietic stem cells", Blood, (Nov. 1, 2003), vol. 102, No. 9, pp. 3172-3178.

A

B

D

A

B

COMPOSITIONS AND METHODS FOR THE EXPANSION OF STEM CELLS

CROSS REFERENCE TO RELATED APPLICATIONS

This application claims priority from U.S. Provisional Application No. 61/758,541, filed Jan. 30, 2013, the entire contents of which are incorporated herein by reference.

STATEMENT REGARDING FEDERALLY SPONSORED RESEARCH

This invention was made with Government support under Grant Numbers CA118085 and CA098210 awarded by National Institutes of Health. The United States Government has certain rights in the invention.

FIELD OF THE DISCLOSURE

The present disclosure relates to methods for expansion of stem cell populations using a polypeptide that enhances stem cell growth and proliferation, and maintains the stemness of cells during expansion. The present disclosure further relates to novel homeobox protein mutants (e.g., HOXA9 and HOXB4 mutant proteins) and the use thereof to expand certain stem cell populations. The present disclosure also provides methods for treating a subject having a disease or disorder which requires a stem cell based therapy.

INCORPORATION BY REFERENCE OF SEQUENCE LISTING

The Sequence Listing in an ASCII text file, named as 29727_4849_03_SequenceListing.txt of 15.2 KB, created on Jul. 29, 2015, and submitted to the United States Patent and Trademark Office via EFS-Web, is incorporated herein by reference.

BACKGROUND OF THE DISCLOSURE

Stem cells develop into several different cell types. Primarily, stem cells fall under two categories: embryonic and adult. In a developing embryo, stem cells differentiate into specialized embryonic tissues. In adult organisms, stem cells and progenitor cells act as a repair system for the body, replenishing specialized cells, but also maintain the normal turnover of regenerative organs, such as blood, skin, or intestinal tissues. Adult stem cells can differentiate into multiple pathways. Mesenchymal stem cells are adult stem cells which give rise to a variety of cell types including, bone cells (osteocytes), cartilage cells (chondrocytes), fat cells (adipocytes), and connective tissue (i.e., tendons). Neural stem cells are adult stem cells in the brain which give rise to its three major cell types: neurons; astrocytes and oligodendrocytes. Epithelial stem cells are adult stem cells in the lining of the digestive tract occur in deep crypts. Skin stem cells are adult stem cells which occur in the basal layer of the epidermis and at the base of hair follicles.

Hematopoietic stem cells (HSCs) are pluripotent, asymmetrically self-renewing cells that give rise to all mature blood cells through successive rounds of differentiation. Specifically, HSCs have been identified in fetal bone marrow, fetal liver, umbilical cord blood (UCB), adult bone marrow, and peripheral blood following treatment with recombinant human granulocyte colony-stimulating factor (G-CSF), which are capable of differentiating into three cell lineages including myeloerythroid (i.e., red blood cells, granulocytes, monocytes), megakaryocyte (i.e., platelets) and lymphoid (i.e., T-cells, B-cells, and natural killer) cells. These HSCs are used in clinical transplantation protocols to treat a variety of diseases including malignant and non-malignant disorders. Currently, HSC transplantation is used to treat hematological diseases, such as leukemia and bone marrow failure. Expansion of HSCs would improve transplantation outcomes and help meet the demand for stem cell transplants by permitting the use of samples of limited quantity (e.g., cord blood) or with low total numbers of HSCs (e.g., poor HSC mobilizers). However, the relative inability to expand HSCs imposes a major limitation on the current use of HSC transplantation, and thus there is a shortage of HSCs for patient treatments.

The signals that govern the self-renewal process have been intensively pursued in order to facilitate HSC expansion by transiently enforcing proliferation pathways or blocking differentiation cues, which would be highly desirable as a means to augment the number of HSCs for transplantation. Human studies reveal that adult HSCs can undergo repeated rounds of asymmetric self-renewal with maintenance of the stem cell pool but with little or no expansion. In contrast, fetal and neonatal stem cells can be maintained in culture for 2-3 months with absolute increases in the number of HSCs. See Ando, K. et al., Blood. 2006; 107(8):3371-3377; and Dahlberg, A. et al., Blood. 2011; 117(23):6083-6090.

Homeobox (HOX) genes encode transcription factors that regulate patterning during embryonic development, and hematopoiesis both pre- and post-natally. In early development, HOX gene expression is both temporally and spatially regulated, as reflected by the sequential order of transcription with respect to their 3' to 5' chromosomal position. However, the spatio-temporal regulation of HOX gene expression is not observed in hematopoiesis, but instead assumes a complex, overlapping expression pattern that is not lineage-specific. Certain HOX genes, are highly expressed in HSCs and progenitor cells, and are generally downregulated as cells terminally differentiate into mature, lineage-specific blood cells. See Sauvageau, G et al., Proc Natl Acad Sci USA. 1994; 91(25):12223-12227. However, to date, the mechanisms underlying transcriptional regulation of HOX genes during hematopoiesis remain largely unknown.

The identification of HOX genes that are highly expressed in $CD34^+$ HSCs and early progenitors led to the discovery that HOXB4 expression by retroviral transduction promoted the selective expansion of murine HSCs in cell culture and following bone marrow transplantation. See Sauvageau, G et al., Genes Dev. 1995; 9(14):1753-1765. Moreover, the enhanced proliferation of HOXB4-transduced HSCs did not alter HSC differentiation. See Thorsteinsdottir, U. et al., Blood. 1999; 94(8):2605-2612; and Antonchuk, J. et al., Cell. 2002; 109(1):39-45.

Conversely, when other HOX genes, such as HOXA9 were constitutively expressed in HSCs instances of myeloid leukemia developed. See Kroon, E. et al., Embo J. 1998; 17(13):3714-3725; and Care, A. et al., 1999; 18(11):1993-2001. Moreover, when the effects of HOX protein overexpression in different species were analyzed species-specific variations in the magnitude of HOX-induced HSC proliferation were observed. Specifically, modest effects observed in cells from humans and baboons when compared to those of mice and dogs. See Zhang, X B et al., J Clin Invest. 2008; 118(4):1502-1510. Additional studies revealed the development of myeloid leukemia in large mammals two years post-transplantation with HSCs expressing retrovirally-transduced HOXB4, highlighting the risks of such genetic manipulation. See Zhang, X B., *J Clin Invest.* 2008; 118(4): 1502-1510. Taken together, current research indicates that ectopic HOX expression is not likely to produce an HSC expansion method capable of promoting HSC proliferation at a level necessary to create therapeutically significant amount of HSCs.

Therefore, a transient delivery method to augment HOX expression levels in HSCs is necessary for potential human therapeutic applications. To that end, direct protein transduction methods resulted in comparable levels of ex vivo murine HSC proliferation when compared with retroviral integration, but the short half-life of HOX protein necessitated frequent replenishing of the recombinant protein, which is impractical for large-scale ex vivo expansion of HSCs. See Krosl, J. et al., *Nat Med.* 2003; 9(11):1428-1432. Recently, studies have sought to stabilize the HOXB4 protein by modifying the N-terminal domain of the native peptide. See U.S. Pat. No. 8,039,463. However, while mutations in the N-terminal resulted in an increase in protein stability, such mutants were incapable of outcompeting wild-type HOXB4 protein, resulting in reduced long-term repopulation capabilities.

SUMMARY OF THE DISCLOSURE

A number of HOX proteins, including the HOXB4 and HOXA9 proteins, are subjected to ubiquitination and subsequent degradation by CUL4 ubiquitin ligase. The present disclosure has identified a degradation signal (degron) within the first alpha helix of the HOX protein HD region. Specifically, the degron includes a Lysine-Glutamic acid-Xaa-Glutamic acid ("LEXE motif" [SEQ ID NO: 2]) sequence within the first alpha helical domain of the HOX protein HD region. The present disclosure has also determined that mutations within the LEXE motif result in profound stabilization of a HOX protein. Accordingly, mutant HOX (or "HOX(m)") proteins and use thereof in expanding stem cells are provided in this disclosure.

In some embodiments, the HOX(m) protein is a HOXB4 (m) protein. The HD region of the human HOXB4 protein is composed of amino acids 163-221, with the LEXE motif located at positions 175-178. In a specific embodiment, a HOXB4(m) protein of the present disclosure includes an amino acid substitution at at least one of the positions: 175, 176, 178, e.g., as set forth in SEQ ID NO: 3. In certain aspects of the disclosure, HOXB4(m) proteins contain amino acid mutations in at least two of amino acids 175, 176, 178 within the LEXE motif of the HOXB4 polypeptide—that is, at least two of the three conserved amino acids, L175, E176 and E178 have been mutated, (e.g., substituted). In other embodiments, HOXB4(m) proteins contain amino acid mutations in all three of the conserved amino acids within the LEXE motif.

In other embodiments, the HOX(m) protein is a HOXA9 (m) protein. The HD region of the human HOXA9 protein is composed of amino acids 207-263, with the LEXE motif located at positions 219-222. In a specific embodiment, a HOXA9(m) protein of the present disclosure includes an amino acid substitution at at least one of the positions: 219, 220, 222 e.g., as set forth in SEQ ID NO: 6. In certain aspects of the disclosure, HOXA9(m) proteins contain amino acid mutations in at least two of amino acids 219, 220, 222 within the LEXE motif of the wild-type HOXA9 protein—that is, at least two of the three conserved amino acids, L219, E220 and E222 have been mutated, (e.g., substituted). In other embodiments, HOXA9(m) proteins contain amino acid mutations in all three of the conserved amino acids within the LEXE motif.

The HOX(m) proteins disclosed herein possess unique characteristics. For example, the HOXB4 and HOXA9 mutant proteins of the instant disclosure have a longer lifetime in cells than their wild-type HOX protein counterparts because the novel mutant proteins include mutations with the degron region of the homeodomain of the wild-type HOX protein (e.g., LEXE motif), which inhibits post translational regulation of the HOX protein by CUL4 ubiquitin ligase. Specifically, mutations of the LEXE motif of the HOXB4 or HOXA9 protein have been demonstrated herein to prohibit interaction between CUL4A ubiquitin ligase and the first alpha helical domain of the HOXB4 or HOXA9 protein homeodomain. Therefore, HOX(m) proteins having mutations in the LEXE motif are degradation resistant proteins and are present for longer periods of time than wild-type HOX proteins.

In other embodiments, the present disclosure provides a method for expanding a stem cell population, based on providing to the stem cell population a HOX(m) protein in an amount effective to expand the stem cell population. In certain embodiments, the HOX(m) polypeptide is a HOXB4 (m) protein. In other specific embodiments, the HOX(m) polypeptide is a HOXA9(m) protein.

The current disclosure further provides a method for treatment of diseases, disorders, or abnormalities in a subject requiring a stem cell based therapy. In one non-limiting embodiment, the method of treatment includes transplanting a therapeutically effective amount of a stem cell population which has been expanded in the presence of a HOX(m) protein, to a subject in need of the transplantation.

DETAILED DESCRIPTION OF THE DISCLOSURE

Figure 1:
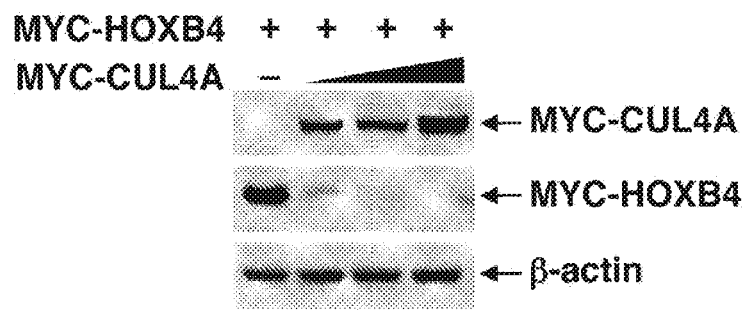
FIG. 1. CUL4A targets HOXB4 for ubiquitin-dependent degradation. A. Steady-state levels of MYC-HOXB4 were determined in response to increasing levels of co-transfected MYC-CUL4A in 293T cells by immunoblotting with the anti-MYC and β-actin (loading control) antibodies. B. Pulse-chase analysis of HOXB4 half-life was performed following shCUL4A knockdown. C. In vivo ubiquitination of HOXB4 in response to increasing levels of dominant-negative CUL4A was detected in 293T cells following transfection with the indicated plasmids, treatment with MG132, precipitation with $Ni^{2+}$-NTA agarose beads under denaturing conditions and immunoblotting with anti-MYC antibody. D. To determine the physiological effect of CUL4A and CUL4B on endogenous HOXB4 protein levels, bone marrow stem and progenitor cells from Cul4a and Cul4b knockout mice and their wild-type littermates were purified and analyzed by immunoblotting with anti-HOXB4. The upper panel showed the genotyping of $Cul4a^{-/-}$ and $Cul4b^{-/Y}$ mice by PCR. E. HeLa cells were transfected with 6 mg shCONTROL or 6 mg shCUL4A plasmids for 48 hours, and subjected to SDS-PAGE and immunoblotting with the anti-CU4A antibody. β-actin levels were determined as a loading control.
Figure 1:
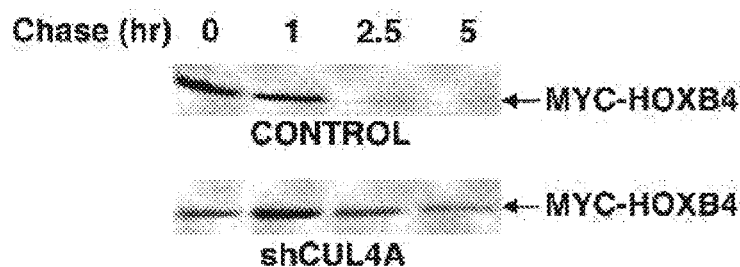
Figure 1:
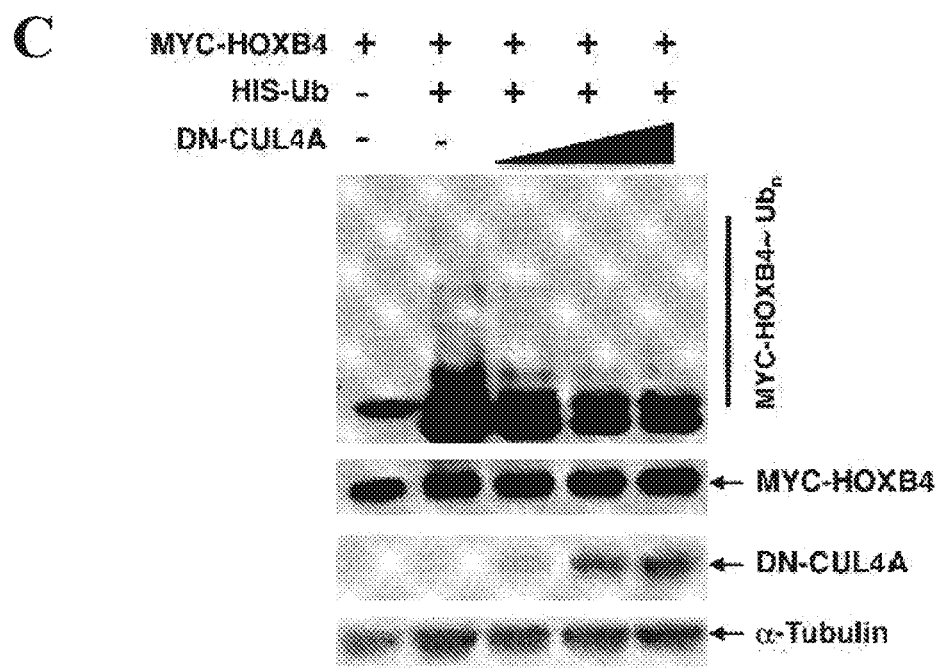
Figure 1:
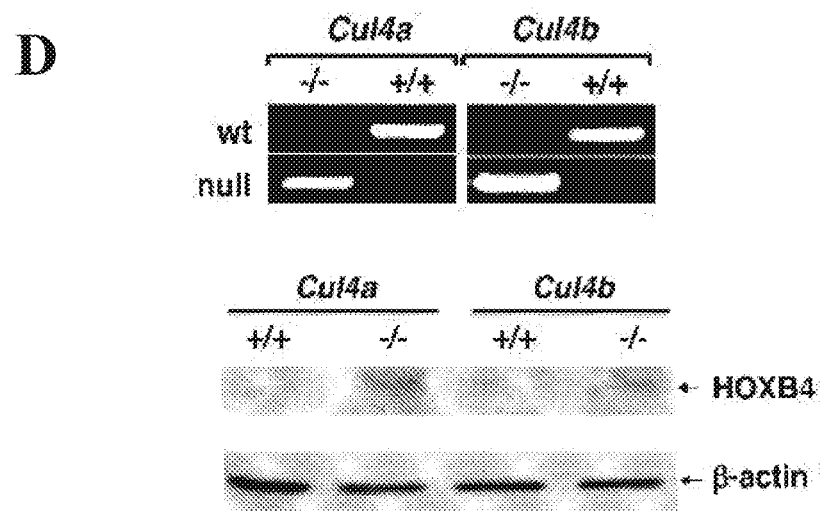
Figure 1:
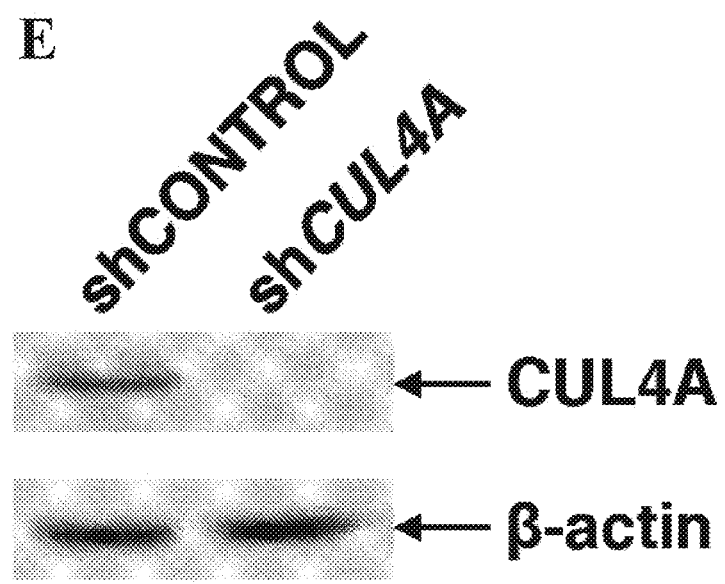

Before the present composition and methods are described, it is to be understood that the present disclosure is not limited to the particular compositions, methods, and experimental conditions described, as such compositions, methods, and conditions may vary. It is also to be understood that the terminology used herein is for purposes of describing particular embodiments only, and is not intended to be limiting.

Isolated HOX Mutant Proteins

The term "peptide" or "protein" or "polypeptide" refers to a linear series of amino acid residues linked to one another by peptide bonds between the alpha-amino and carboxyl groups of adjacent amino acid residues.

The term "isolated" and "purified", when used in reference to a molecule (such as a peptide, protein or polypeptide), means that the molecule has been removed from its naturally occurring environment and is substantially free of other molecules (such as other proteins). By "substantially free" of other proteins, it is meant that a protein of interest accounts for at least 60%, 70%, 80%, 90%, or 95% (by dry weight) of total proteins in a composition. When an isolated protein is recombinantly produced, it can also be substantially free of culture medium, i.e., culture medium represents less than about 20% of the volume of the protein preparation, less than about 10% of the volume of the protein preparation or less than about 5% of the volume of the protein preparation. For example, the proteins of the present disclosure can be purified to homogeneity or other varying degrees of purity. The level of purification can be based on the intended use. In certain non-limiting examples, an isolated HOX mutant protein can be purified from cells that express such mutant protein, as further described below, or can be synthetically made using known protein synthesis methods.

Homeobox (HOX) proteins are a family of transcription factors that, when active, promote proliferation of certain stem cell populations. HOX proteins are regulated post-translationally by ubiquitin ligases (i.e., CUL4A and CUL4B) through interaction with a binding domain present in the homeodomain region of HOX peptides. Specifically, when CUL4A interacts with a HOX protein the HOX transcription factor is ubiquitinated and subject to proteosome-mediated degradation. HOX protein family members contain a highly conserved homeodomain region (HD), which includes three separate alpha helical domains, the first of which contains a degron domain, which faces away from DNA when a functional HOX protein is bound to DNA by the second alpha helical domain of o the HOX HD region. Non-limiting examples of a HOX protein HD region includes the human HOXB4 protein homeodomain (HOXB4 HD) region spanning amino acids 163-221. Similarly, the human HOXA9 protein contains a highly conserved homeodomain (HOXA9 HD) region spanning amino acids 207-263.

The term "wild-type HOX protein(s)" or "HOX protein(s)" as used in the current disclosure shall mean a homeobox protein family member, regardless of the organism from which said HOX protein originates, which includes a conserved LEXE motif within the within the first alpha helix of the HOX protein HD region. Non-limiting examples of wild-type HOX proteins include: HOXA1 (NP_005513.1), HOXA2 (NP_006726.1), HOXB4 (AAG45052.1, NP_076920 or NP_076920.1), (HOXB7 (NP_004493.3), HOXA9 (NP_689952.1), (HOXB9 (NP_076921, NP_076921.1), HOXA11 (NP_005514.1), HOXA13 (AAC50993, NP_000513.2), and homologs thereof. As used herein the term "homolog" shall mean the orthologs of a human HOX gene or protein in non-human vertebrate species. For example, homologs of human HOXB4 refer to HOXB4 from non-human vertebrate species. In certain embodiments, homologs of a human wild type HOX protein have an amino acid sequence substantially identical to the human wild-type HOX protein, i.e., at least 80-85%, at least 90-95% or more sequence identity. Further, homologs of a human HOX protein retain the same function as the human HOX protein, e.g., the ability to modulate CUL4 mediated HOX protein degradation.

More specifically, the term "HOXB4" or "wild-type HOXB4" as referred to in the current disclosure is a member of the Antp homeobox family also known as homeobox B4, HOX2, HOX2F and HOX-2.6, and encodes a nuclear protein with a homeobox DNA binding domain. The human HOXB4 gene is located on human chromosome 17 (q21.32) comprising 2,875 base pairs. The term "HOXB4 gene" includes the nucleic acid molecule represented by NC 000017.10 (human HOXB4). The HOXB4 gene is highly conserved in chimpanzee, dog, cow, mouse, rat and chicken, and thus the term "HOXB4 gene" also includes homologs of the human HOXB4 gene in these other mammalian species.

The HOXB4 gene produces an mRNA transcript, including NM_24015 and NM_024015.4, which translate into "HOXB4 protein" or "wild-type HOXB4 protein" or "HOXB4 polypeptide", which is represented by AAG45052.1 or NP_076920.1. The amino acid sequence of the 251 amino acid wild-type HOXB4 protein from human is set forth in SEQ ID NO: 1.

Another example of a HOX wild-type protein is the "HOXA9 protein" or "wild-type HOXA9 protein", which is represented by NP_689952.1. The amino acid sequence of the 272 amino acid wild-type HOXB4 protein from human is set forth in SEQ ID NO: 5. The HOXA protein is the product of a homeobox A9 or "HOXA9 gene", which is located on chromosome 7 (NC_000007.13) and encodes a DNA binding transcription factor. The term "HOXA9 gene" includes the nucleic acid molecule represented by NG_029923.1, which translates into the HOXA9 protein (NP_689952.1) as set forth in SEQ ID NO: 5. The HOXA9 gene is highly conserved in chimpanzee, Rhesus monkey, dog, cow, mouse, rat, chicken, and zebrafish, and thus the term "HOXA9 gene" also includes homologs of the human HOXA9 gene from these other animal species.

The term "variant" as used herein refers to nucleic acid molecules having one or more alterations in the sequence of a gene, transcript or protein which naturally occur in a population. For example, a gene variant or protein variant may share a sequence identity of at least 90%, 95%, 98%, 99%, or greater to a reported or specified nucleotide or protein sequence, respectively.

A number of HOX proteins, including the HOXB4 and HOXA9 proteins are subjected to ubiquitination and subsequent degradation by CUL4 ubiquitin ligase. The present disclosure has identified a degradation signal (degron) within the first alpha helix of the HOX protein HD region. Specifically, the degron includes a Lysine-Glutamic acid-Xaa-Glutamic acid ("LEXE motif" [SEQ ID NO: 2]) sequence within the first alpha helical domain of the HOX protein HD region, where Xaa can be any of the following amino acids: Alanine (A), Arginine (R), Methionine (M), Asparagine (N), Aspartate (D), Cysteine (C), Glutamine (Q), Glutamate (E), Glycine (G), Histidine (H), Isoleucine (I), Leucine (L), Lysine (K), Phenylalanine (F), Proline (P), Serine (S), Threonine (T), Tryptophan (W), Tyrosine (Y) or Valine (V). The LEXE motif is located at amino acids 175-178 of the human wild-type HOXB4 protein. The LEXE motif of the human HOXA9 protein is found from amino acids 219-222.

In accordance with the present disclosure, mutations of the LEXE motif can lead to a profound stabilization of HOX protein levels as a result of decreased CUL4 mediated HOX protein degradation.

The term "degradation resistant" or "resistant to proteasome degradation", as referred to in the instant disclosure, shall mean a protein, specifically a HOX protein that is not susceptible to ubiquitin-proteasome degradation, or is associated with reduced ubiquitin-proteasome degradation as compared to a wild type HOX protein. In one aspect of the present disclosure, a degradation resistant protein is not post-translationally regulated by ubiquitin ligases (e.g., CUL4A).

In certain embodiments, degradation resistant HOX mutant proteins are provided ("HOX(m) proteins" or "mutant HOX proteins"). In certain aspects of the present disclosure, degradation resistant HOXB4 mutant proteins ("HOXB4(m)") are provided. In other aspects, degradation resistant HOXA9 mutant proteins ("HOXA9(m)") are provided. These mutant HOX proteins are significantly more stable in cells and are associated with reduced proteasome mediated degradation. Protein stability may be assessed by measuring the amount of protein expressed in a cell and comparing such amount to that of the wild-type over time. For example, a more stable protein is less prone or susceptible to proteasome mediated degradation when compared to a wild-type protein. For example, a "more stable" protein or "degradation resistant" protein may exhibit a 1-fold, 2-fold, 3-fold, 4-fold, 5-fold or greater, increase in the amount of the protein over the level of a wild type HOX protein at a selected time point. Alternatively, a degradation resistant protein is characterized by a longer half life as compared to a wild type (unmodified) protein.

Protein stability may be measured by any number of known methods, including but not limited to Western blot or protein microarray, which detect the amount of protein present in a cell or cells over a period of time. For example, cells or cell lines may be established having the same ratio of marker proteins (e.g., (3-actin). Such cells are then transfected or provided with an equal amount of either wild-type protein (e.g., wild-type HOXB4) or a mutant protein (HOXB4(m)) and cultured for an equal period of time. The ratio of marker protein in the cells expressing wild-type protein is then compared to the expression of marker protein in the cells expressing mutant protein and then a comparison is made between this ratio and the ratio obtained when amount of wild-type and mutant proteins are measured. Using this comparison, it may be concluded that the stability of a mutant protein has been altered if the ratio determined in cells expressing wild-type protein is different than the ratio determined in cells expressing mutant protein. For example, in cases where the ratio of wild-type protein is lower than the ratio of mutant protein, the mutant protein is more stable.

In another example, protein stability may be measured by determining the half-life of a mutant protein relative to wild-type. Methods for determining the half-life of a protein are well known by those of ordinary skill in the art and any such method may be used in conjunction with the present disclosure. A non-limiting example of determining protein half-life is the pulse-chase assay. For example, cells are cultured and transfected or incubated with a metabolically or biosynthetically labeled protein ($^{35}$S, $^{3}$H, or $^{14}$C) e.g., wild-type HOX or HOX mutant proteins. These cells are then subjected to subsequent a "chase" period, whereby cells are further incubated with the unlabeled counterpart of the precursor protein used for labeling. Samples are harvested and proteins are immunopreciptiated, separated by SDS PAGE and the levels of labeled protein is determined. By comparing the level of labeled protein at 0 hour to those "chased" (e.g.: 60 min) provides an indication of the rate of protein turnover, and thus protein half-life.

More specifically, protein stability can be determined by transient transfection of cells, e.g., HeLa cells or 293T cells by calcium phosphate precipitation (Promega) or by Fugene 6 reagent (Roche) using expression plasmids (i.e., pGreen Lantern-1) to express μg quantities of a specific HOX mutant protein and a wild-type protein. The total amount of DNA is then normalized in each transfection using the pcDNA3 expression vector. A 2 μg aliquot of pGREEN LANTERN-1 plasmid can be included in all the transient transfection experiments in order to measure the transfection efficiencies and to compare the steady-state levels of transfected proteins. Procedures for immunoblotting, immunoprecipitation, metabolic labeling by [$^{35}$S]methionine and cysteine for pulse-chase analysis of protein half-lives, and in vivo ubiquitylation assay have been comprehensively described and are well known to those of ordinary skill in the art. Briefly, transfected ells are starved in DMEM without methionine and cysteine for 1 hour, pulse-labeled with a mixture of [$^{35}$S]methionine and [$^{35}$S]cysteine (100 μCi/ml) for 30 minutes, and subsequently chased in DMEM with an excess of methionine (~3 mM) and cysteine (~1 mM) over a period of time, e.g., 0.5-5 hours. At each time point, cells are lysed in lysis buffer (e.g., 150 mM NaCl, 1.0% Nonidet P-40, 50 mM Tris, pH 8.0) plus protease inhibitors (PharMingen). Equivalent amount of wild-type and mutant HOX protein containing extracts were immunoprecipitated twice with monoclonal antibodies and resolved on 9% SDS-PAGE. The amount of $^{35}$S-labeled mutant and wild-type HOX protein at each time point is then visualized and quantitated by PhosphorImager scanning (Molecular Dynamics, Inc.). The half-life of the endogenous HOX protein in such cells or transfected mutant protein in cells are then measured similarly using separate antibodies. To evaluate the effect of UV irradiation on the stability of wild-type HOX or HOX mutant proteins, cells were irradiated with UV at 10 J/m$^2$ followed by recovery in DMEM for 8 h prior to pulse-chase analysis. In some instances, 100 μM MG132 proteasome inhibitor (Peptide International) was included in the chase medium, and the stability of mutant HOX proteins can be observed.

In particular embodiments, the mutant HOX proteins of the present disclosure contain point mutations within the LEXE motif of the HOX HD region. In a specific aspect, the HOX(m) protein is a HOXB4(m) protein. In one embodiment, the HOXB4(m) protein includes an amino acid substitution at at least one of the positions: 175, 176, 178, e.g., as set forth in SEQ ID NO: 3. In another embodiment, the HOXB4(m) protein contains amino acid mutations in at least two of amino acids 175, 176, 178 within the LEXE motif of the HOXB4 polypeptide—that is, at least two of the three conserved amino acids, L175, E176 and E178 have been mutated, (e.g., substituted). In other embodiments, the HOXB4(m) protein contains amino acid mutations in all three of the conserved amino acids within the LEXE motif.

In another aspect, the HOX(m) protein is a HOXA9(m) protein. In a specific embodiment, a HOXA9(m) protein of the present disclosure includes an amino acid substitution at at least one of the positions: 219, 220, 222, e.g., as set forth in SEQ ID NO: 6. In other embodiments, HOXA9(m) proteins contain amino acid mutations in at least two of amino acids 219, 220, 222 within the LEXE motif of the wild-type HOXA9 protein—that is, at least two of the three conserved amino acids, 219, 220, 222 have been mutated, (e.g., substituted). In still other embodiments, HOXA9(m) proteins contain amino acid mutations in all three of the conserved amino acids within the LEXE motif.

In many embodiments, the mutations in at least two or all three of the conserved amino acids within the LEXE motif are non-conservative substitutions. The term "non-conservative substitutions", as used herein shall mean the substitution (i.e., point mutation) of one amino acid by another which has different properties (i.e, charge, polarity, hydrophobicity). Examples of a conservative substitution include the substitution of a hydrophobic residue such as isoleucine, valine, leucine, alanine, phenylalanine, tyrosine, tryptophan or methionine for a polar or charged amino acid residue such as lysine, arginine, glutamine, asparagine, aspartate, glutamate, histidine serine, threonine, or cysteine. Likewise, the present disclosure contemplates the substitution a charged amino acid such as lysine, arginine, histidine, aspartate and glutamate for an uncharged residue including, but not limited to serine, threonine, asparagines, glutamine, or glycine. In certain embodiments, non-conservative substitutions include the substitution of an uncharged, hydrophobic amino acid such as leucine with a charged amino acid such as, aspartic acid, lysine, arginine, or glutamate. For example, L175 in HOXB4 or L219 in HOXA9 can be substituted with a charged amino acid, such as a positively charged amino acid (Arg, His, or Lys) or a negatively charged amino acid (Asp or Glu). In a specific embodiment, the non-conservative amino acid substitution includes the replacement of a negatively charged residue (i.e., glutamate) with a positively charged amino acid such as lysine, histidine or arginine. A non-limiting example of a HOX mutant protein of the present disclosure includes, a HOXB4(m) protein having amino acid substitutions, L175D, E176K and E178K, e.g., as in SEQ. ID. NO: 4. Another non-limiting example of a HOX mutant protein of the present disclosure includes amino acid substitutions L219D, E220K and E222K, e.g., as in SEQ ID NO:7.

In accordance with the present invention, the same or similar substitutions can be made in wild-type HOX proteins from species other than human to obtain stabilized HOX mutant proteins. In certain embodiments, the HOXB4 protein from other animal species, such as mice, chimpanzee, dog, cow, mouse, rat, chicken, or zebrafish, can be mutated by substitutions with in LEXE motif, similar to the substitutions described above for the human HOXB4 protein. In another embodiment, the HOXA9 protein from other animal species, such as mice chimpanzee, dog, cow, mouse, rat, chicken, or zebrafish, can be mutated by substitutions with in LEXE motif, similar to the substitutions described above for human HOXA9.

Isolated or purified HOX(m) proteins can be obtained by various means, including various recombinant expression systems. A nucleic acid molecule encoding a mutant HOX protein can be cloned into an expression vector, which is then introduced into a host cell for protein expression.

A variety of expression/host systems may be utilized. These systems include, but are not limited to, microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562, 32D cells and 293 cells. Mammalian host cells may be preferred when post-translational modifications such as glycosylation and polypeptide processing are important for activity. Mammalian expression allows for the production of secreted or soluble polypeptides which may be recovered from the growth medium.

Using an appropriate host-vector system, HOX mutant proteins are produced recombinantly by culturing a host cell transformed with an expression vector containing the nucleic acid molecules of the present disclosure under conditions allowing for production. Transformed cells can be used for long-term, high-yield protein production. Once such cells are transformed with vectors that contain selectable markers as well as the desired expression cassette, the cells can be allowed to grow for one to two days in an enriched media before they are switched to selective media. The selectable marker is designed to allow growth and recovery of cells that successfully express the introduced sequences. Resistant clumps of stably transformed cells can be proliferated using tissue culture techniques appropriate to the cell line employed. The protein can then be isolated from the cells by an appropriate purification scheme using protein purification techniques known by one of ordinary skill in the art.

In certain embodiments, the protein purification techniques involve, at one level, fractionation of the proteinaceous and non-proteinaceous fractions. Having separated the polypeptides from other materials, the polypeptide of interest can be further purified using chromatographic and electrophoretic techniques to achieve partial or complete purification (or purification to homogeneity). Analytical methods particularly suited to the preparation of polypeptides or the present invention include, but are not limited to, ion-exchange chromatography, exclusion chromatography; polyacrylamide gel electrophoresis; isoelectric focusing.

Various techniques suitable for use in purification will be well known to those of skill in the art. These include, for example, chromatography, HPLC, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Various methods for quantifying the degree of purification of a polypeptide are known to those of skill in the art. These include, for example, determining the specific binding activity of an active fraction, or assessing the amount of the polypeptide within a fraction by SDS/PAGE analysis. A exemplary method for assessing the purity of a polypeptide fraction is to calculate the binding activity of the fraction, to compare it to the binding activity of the initial extract, and to thus calculate the degree of purification, herein assessed by a "fold purification number." The actual units used to represent the amount of binding activity will be dependent upon the particular assay technique chosen to follow the purification and whether or not the polypeptide exhibits a detectable binding activity.

Methods for Expanding Stem Cells

The HOX(m) proteins disclosed herein possess unique characteristics. For example, the subject HOXB4 and HOXA9 mutant proteins have a longer lifetime in cells than their wild-type HOX protein counterparts because the novel HOX mutant proteins include mutations within the degron region of the homeodomain of the HOX protein (e.g., LEXE motif). Mutations within the degron inhibit post translational regulation of the HOX protein by CUL4 ubiquitin ligase. For example, mutation of the LEXE motif of the HOXB4 or HOXA9 protein prohibits interaction between CUL4A ubiquitin ligase and the first alpha helical domain of the HOXB4 or HOXA9 protein homeodomain. Therefore, the HOXB4 or HOXA9 mutant proteins of the present disclosure are degradation resistant proteins because the subject mutant proteins are present for longer periods of time than wild-type HOXB4 or wild-type HOXA9 due to modification of the LEXE motif, which inhibits CUL4A mediated degradation.

The present disclosure provides a method for expanding a stem cell population, based on providing to the stem cell population a HOX(m) polypeptide in an amount effective to expand the stem cell population. In certain embodiments, the HOX(m) polypeptide is a HOXB4(m) protein. In a specific embodiment, the HOX(m) polypeptide is a HOXA9(m) protein.

"Expanding" or "expansion" as used herein refers to increasing the number of stem cells by proliferation of existing stem cells in a heterogeneous or homogenous population of cells, instead of converting cells which are not stem cells (i.e., terminally differentiated cells) into stem cells.

The term "amount effective" or "effective amount" means the amount of the subject peptide or material that will elicit the biological or medical response of a cell, tissue, system, animal or human that is being sought by the researcher, veterinarian, medical doctor or other clinician. For example, an effective amount of a HOX(m) protein provided to a cell can be the amount necessary to increase proliferation of such cells. The precise amount depends on the particular approach employed to provide the HOX(m) protein.

In certain embodiments, the HOX(m) protein is provided to a stem cell population using a nucleic acid based approach. In one aspect, an exogenous HOX(m) gene is transiently expressed in a stem cell population, which is then transcribed and translated using endogenous cellular machinery. For example, a nucleic acid encoding a HOX(m) protein is introduced into a stem cell population by transduction, transfection or electrocorporation methods, which are well known by those of ordinary skill in the art.

In some embodiments, the nucleic acid encoding a HOX(m) protein which is introduced into the cells is carried on a vector. Different types of vectors or constructs can be used for transduction or transformation of stem cells. These include plasmid or viral vectors. The term "viral vector" means a vector that comprises all or parts of a viral genome which is capable of being introduced into cells and expressed. Such viral vectors may include native, mutant or recombinant viruses. Such viruses may have an RNA or DNA genome. Examples of suitable viral vectors include, but are not limited to, adenoviruses, adeno-associated virus (AAV), baculoviruses, parvoviruses, herpesviruses, poxviruses, Semliki Forest viruses, vaccinia viruses, and retroviruses and hybrid vectors. Retroviral vectors have been used widely in gene therapy, particularly those based on Moloney murine leukemia virus (MoMLV) to express genes and/or proteins of interest in a host organism or cell population. Additionally, vectors based on murine retroviruses can be used for high efficiency transduction of cells. However, the transduction of human cells with murine retroviral based vectors requires activation of the cells to permit expression. The following non-exhaustive list provides several examples of means for expressing proteins within a population of cells, including but not limited to stem cells.

Integrating vectors, such as retrovirus or lentivirus, are often used for gene therapy, and thus can be used in conjunction with the disclosed methods to express HOXB4 mutant protein. In one embodiment, lentiviral vectors, which are a subclass of the retroviral vectors, can be used for high-efficiency transduction (see, for example, Haas et al., 2000; Miyoshi et al., 1999; Case et al., 1999) and are also capable of transducing non-dividing cells. Therefore, lentiviral vectors do not require the induction of cells into cell cycle, and thus would avoid the loss of pluripotency that cell-cycle induction might cause in some of the cells. Other groups of retroviruses such as spumaviruses, for example the foamy viruses are also capable of efficiently transducing non-dividing cells.

Other types of viral vectors that can be used in the present methods include adenoviral vectors (see Fan et al., 2000; Knaan-Shanzer et al., 2001; and Marini et al. 2000), adeno-associated viral (AAV) vectors (see Fisher-Adams et al., 1996), SV40 based vectors (see Strayer et al., 2000), or forms of hybrid vectors. See, for example, Feng et al., 1997. Adenoviral vectors can be readily produced at high titers and can also transduce non-dividing cells.

In certain embodiments, AAV vectors are used to express HOX(m) proteins in a population of cells. AAV vectors are non-pathogenic, transduce both proliferating and non-proliferating cells including CD34+ cells, and integrate stably into the cellular genome. See Grimm and Kleinschmidt (1999). Moreover, AAV vectors do not induce a host immune response and can be produced in helper-free systems. AAV vectors can effectively transduce CD34+ cells in long-term cultures. See Chaterjee et al., (1999).

In other embodiments, non-integrating methods, such as adenovirus, baculovirus, or transient transfection of plasmids capable of episomal expression, are used to express exogenous proteins. In certain aspects of the disclosure, vectors which result in non-integration of the introduced gene into the cell genome are preferred. In other aspects, viral vectors which allow transient expression of the introduced gene are preferred. In yet other aspects, vectors which have a short life-cycle in the host cell are preferred.

In specific embodiments, HOXA9(m) proteins are expressed using a vector that does not result in the constitutive expression of HOXA9(m) proteins. Specific, non-limiting examples of such vectors, for use in conjunction with the expression of HOXA9(m) proteins include PINCO, MIGR1, and pRS.

In one embodiment, mutant HOX genes of the present disclosure are expressed under the control of a constitutive promoter. Naturally-occurring constitutive promoters control the expression of essential cell functions. As a result, a gene under the control of a constitutive promoter is expressed under all conditions of cell growth. Exemplary constitutive promoters for use in the methods of the present disclosure include, but are not limited to the promoters for the following genes which encode certain constitutive or "housekeeping" functions: hypoxanthine phosphoribosyl transferase (UPRT), dihydrofolate reductase (DHFR) (see Scharfmann et al., *Proc. Natl. Acad. Sci. USA*, (1991) 88:4626-4630), adenosine deaminase, phospho glycerol kinase (PGK), pyruvate kinase, phospho glycerol mutase, the actin promoter (see Lai et al., *Proc. Natl. Acad. Sci. USA*, (1989) 86:10006-10010), and other constitutive promoters known to those of skill in the art. In addition, many viral promoters function constitutively in stem cells. Non-limiting examples of such viral promoters include the early and late promoters of SV40; the long terminal repeats (LTRS) of Moloney Leukemia Virus and other retroviruses; and the thymidine kinase promoter of Herpes Simplex Virus. Accordingly, any of the above-referenced constitutive promoters can be used to control transcription of a heterologous gene inserted into a vector or construct. For example, a HOX gene or HOX mutant gene sequence may be inserted into a vector or construct and expression may be driven by a constitutively active promoter to achieve the desired expression of a HOX(m) protein, such as a HOXB4.

In yet another embodiment, mutant HOX genes of the present disclosure are expressed under the control of an inducible promoter. Genes that are under the control of inducible promoters are expressed in the presence of an inducing agent, (e.g., transcription under control of the metallothionein promoter is greatly increased in presence of certain metal ions). Inducible promoters include responsive elements which stimulate transcription when their inducing factors are bound. For example, there are responsive elements for serum factors, steroid hormones, retinoic acid and cyclic AMP. Promoters containing a particular responsive element can be chosen in order to obtain an inducible response and in some cases, the responsive element itself may be attached to a different promoter, thereby conferring inducibility to the recombinant gene e.g., mutant HOX gene. Thus, by selecting the appropriate promoter (constitutive versus inducible; strong versus weak), it is possible to control both the existence and level of expression of an agent in the genetically modified cell. Selection and optimization of these factors for expression of a gene or its product is deemed to be within the scope of one of ordinary skill in the art without undue experimentation, taking into account the above-disclosed factors. Thus, in certain embodiments, a HOX(m) gene is expressed under the control of an inducible promoter and introduced into a population of stem cells.

In other embodiments, as an alternative to a nucleic acid-based approach, a HOX(m) protein is provided to the cells through a protein-based approach, also referred to herein as protein transduction.

Protein transduction is the internalization of proteins into the cell, from the external environment. This process relies on the inherent property of a small number of proteins and peptides of being able to penetrate the cell membrane. The transducing property of these transport moieties can be conferred upon proteins which are expressed as fusions with them. The term "transport moiety" as used herein means a peptide that is capable of crossing a cell membrane and can transport a polypeptide of the present invention into a stem cell.

In a specific embodiment, the transport moiety is part of a HOX(m) protein itself, i.e., inherent or internal in the HOX(m) protein. In this embodiment, a HOX(m) protein is added directly to the stem cell population and traverses the cell membrane from the cellular media via its own transmembrane penetrating activity. See Amsellem S, et al., *Nat. Med.* (2003) 9(11):1423-1427.

In another embodiment, a mutant HOX protein is linked or fused to an exogenous (or heterologous) transport moiety. Examples of such heterologous transport moieties include, but are not limited to, HIV-1 transactivator of transcription (Tat) peptide, a Chariot™ protein, an arginine-rich peptide, an Antennapedia-derived penetratin peptide, a herpes simplex virus type 1 VP22 protein, and a +36 GFP.

Antennapedia Peptide:

The antennapedia motif is derived from a family of *Drosophila* homeoproteins, a class of trans-activating factors involved in the developmental process. These proteins recognize and bind DNA through a 60 amino acid carboxy-terminal region arranged in three-helical sequences, called the homeodomain. The homeodomain of antennapedia (Ant-pHD) is capable of translocating across neuronal membranes and is conveyed to the nucleus.

Herpes Simplex Virus VP22 Protein:

The herpes simplex virus type 1 (HSV-1) VP22 protein is a structural polypeptide forming the major component of the virus tegument situated between the envelope and capsid regions of the mature virion. It is a small basic protein, approximately 38 kDa in size, encoded by the UL49 gene.

HIV TAT Protein Transduction Domain:

The HIV-1 trans-activator gene product, TAT, has been shown to be a regulator of transcription in latent HIV and is essential for HIV replication. It is an 86 amino acid protein made from two exons of 72 and 14 amino acids, respectively.

Chariot Protein:

Chariot is a 2843 dalton peptide and forms a non-covalent complex with the protein of interest (Active Motif, Inc.).

Other non-limiting, examples of peptides that can be used for protein transduction include arginine-rich peptides, +36 GFP and the Mtb carrier domain from *Mycobacterium tuberculosis* Mce1 protein, as described in U.S. Pat. No. 6,399,764 (B1) and 6,072,048.

When a HOX(m) protein is provided to cells through a protein-based approach, the HOX(m) protein can be provided in an amount between 0.1 µg and 10 mg, an amount between 0.1 µs and 5 mg, 0.1 µs and 3 mg, 0.1 µg and 1 mg, 0.1 µg and 0.5 mg, 0.1 µs and 200 µs, 0.1 µs and 100 µs, 0.1 µs and 50 µs, 0.1 µs and 10 µs, 0.1 µs and 5 µs, 0.5 µg and 2 µg. In yet another embodiment 1 µg of isolated HOXB4 (m) or HOXA9(m) protein is provided to a stem cell containing media.

In certain embodiments where a HOX(m) protein is provided to a stem cell population in culture where such cells are targeted for expansion, an appropriate dosage of HOX mutant protein can be between 0.1 µg/mL and 10 mg/mL, for example, 5 mg/mL, 3 mg/mL, 1 mg/mL, 0.5 mg/mL, 200 µg/mL 100 µg/mL, 10 µg/mL, 5 µg/mL 1 µg/mL, or any value between the above listed values. The HOX(m) proteins may be administered to a culture of stem cells on a regimen of 1 to 4 times per day, once or twice per day, or every other day.

In many embodiments the cells used in the present methods of expanding include stem cells or a population thereof. "Stem cell(s)" or "stem cell population" as used herein refers to a cell having the ability to both self-renew and differentiate to produce at least one functional, terminal cell type.

Stem cells of the present disclosure (e.g., adult stem cells, and hematopoietic stem cells) include all those known in the art that have been identified in mammalian organs or tissues. Stem cells may include, but are not limited to pluripotent stem cells, mesenchymal stem cells, hematopoietic stem cells, myeloid stem cells, and lymphoid stem cells. The most well characterized stem cell is the hematopoietic stem cell. The hematopoietic stem cell, isolated from bone marrow, blood, cord blood, fetal liver and yolk sac, is the progenitor cell that generates blood cells or following transplantation reinitiates multiple hematopoietic lineages and can reinitiate hematopoiesis for the life of a recipient. When transplanted into lethally irradiated animals or humans, hematopoietic stem cells can repopulate the erythroid, neutrophil-macrophage, megakaryocyte and lymphoid hematopoietic cell pool.

"Progenitor cell(s)" as used herein refers to a cell having a limited ability to self-renew and which differentiates to produce at least one functional, terminal cell type.

"Hematopoietic cells" as used in the present disclosure refer to cells normally found in the blood as well as cells that give rise to cells normally found in the blood, such as cells found in the bone marrow. In this context "normally" includes the situation where a person is treated to alter the number or quality of cells in the blood or bone marrow. A subset of hematopoietic cells is "hematopoietic stem cells", which as used herein refers to multipotent stem cells that give rise to all blood cell types.

It is well known in the art that hematopoietic cells include multipotent stem cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/ or lymphoid tissue-specific macrophage cell lineage. Hematopoietic stem cell and progenitor cell lineages are discussed in Sieburg et al. 2006, Schroeder et al. 2010, Dykstra et al. 2007, and U.S. Pat. No. 7,994,114, the contents of which are incorporated herein by reference.

Hematopoietic stem cells for use in the methods of the present disclosure can be obtained from blood or blood products. A "blood product" as used herein defines a product obtained from the body or an organ of the body containing cells of hematopoietic origin. Such sources include unfractionated bone marrow, umbilical cord, peripheral blood, liver, thymus, lymph and spleen. Unfractionated blood products can be obtained directly from a donor or retrieved from cryopreservative storage. It will be apparent to those of ordinary skill in the art that all of the aforementioned crude or unfractionated blood products can be enriched for cells having "hematopoietic stem cell" characteristics in a number of ways. For example, the blood product can be depleted from the more differentiated progeny. The more mature, differentiated cells can be selected against, via cell surface molecules they express. Additionally, the blood product can be fractionated and/or sorted by selecting for CD34+ cells.

CD34+ cells are capable of self-renewal and pluripotentiality and selection of such CD34+ cells selection can be accomplished using, for example, commercially available magnetic anti-CD34 beads (Dynal, Lake Success, N.Y.). Additional markers that are exemplary of self-renewal and pluripotency for hematopoietic stem and progenitor cells include, but are not limited to, CD38−/low, SCA-1$^+$, lin$^-$, c-kit$^+$/CD117+, CD59+, Ty1/CD90+.

In one embodiment, the stem cells expanded by the present methods are adult stem cells. In certain embodiments, the stem cells are in or derived from the brain, liver, heart, kidney, skin, pancreas, bladder, gall bladder, large intestine, small intestine, stomach, skeletal muscle, or lung.

In another embodiment, the stem cells are hematopoietic stem cells. In yet another embodiment, the hematopoietic stem cells are obtained or derived from umbilical cord blood, peripheral blood, bone marrow, or spleen. In a specific embodiment, the hematopoietic stem cells are human hematopoietic stem cells.

Hematopoietic stem cells may be harvested or collected prior to expansion of the stem cell population. "Harvesting" hematopoietic progenitor cells is defined as the dislodging or separation of cells from the matrix. This can be accomplished using a number of methods, such as enzymatic, non-enzymatic, centrifugal, electrical, or size-based methods, or preferably, by flushing the cells using media (e.g. media in which the cells are incubated). The cells can be further collected, separated, and further expanded using the subject invention and generating larger populations.

Methods for isolation of hematopoietic stem cells are well-known in the art, and typically involve subsequent purification techniques based on cell surface markers and functional characteristics. The hematopoietic stem and progenitor cells can be isolated from bone marrow, blood, cord blood, fetal liver and yolk sac, and give rise to multiple hematopoietic lineages and can reinitiate hematopoiesis for the life of a recipient. See, for example, U.S. Pat. No. 5,759,793; and 5,716,827. In a non-limiting example of a method of isolating hematopoietic stem and progenitor cells from peripheral blood, blood in PBS is loaded into a tube of Ficoll (Ficoll-Paque, Amersham) and centrifuged at 1500 rpm for 25-30 minutes. After centrifugation the white center ring is collected as the fraction of the original blood sample containing hematopoietic stem cells.

In other embodiments, hematopoietic stem cells are obtained by differentiating embryonic stem cells in culture, or by reprogramming fibroblasts or endothelial cells in culture, as documented in the art. See, e.g., Pereira et al. (*Cell Stem Cell* 13, 205-218, 2013); Wang et al. (*Cell Research* 22, 194-207, 2012); Kaufman (*Blood* 114, 3513-3523, 2009); International Application No. PCT/US14/ 11575; US20090191171 A1 and PCT/US2009/060138.

To directly compare the expansion ability of HSCS and HSCs expressing the HOX mutant proteins of the present disclosure with those expressing wild-type HOX proteins, 15 day liquid cultures were initiated consisting of 10% wt HOXB4 expressing cells, 10% mutated HOX protein expressing cells and 80% non infected cells. At various times, cell cultures were analyzed by flow cytometry for the proportions of YFP (e.g., wild-type HOX expressing) and GFP (e.g., mutant HOX protein expressing) expressing cells. The HOX protein expression in transduced cells will then be evaluated by Western blotting to show that the expression of mutant HOX protein expression correlated with the in vitro expansion of HSC cells. Similarly, cells expressing higher levels of HOX mutant proteins have a greater expansion capacity than those expressing wild-type HOX proteins. See, for example, Example 4 of the current disclosure.

In certain embodiments, methods for expanding a stem cell population include the administration of an effective amount of a HOXB4(m) polypeptide in combination with a stimulating factor. Non-limiting examples of a stimulating factor for use in the methods of the current disclosure include the G-SCF, GM-CSF, M-CSF, a stem cell factor (CD117 or c-Kit), or FMS-like tyrosine kinase-3 (FLT-3) or a cytokine.

In another embodiment, a stem cell population is cultured in a cell growth supporting media. A Non-limiting example of a cell growth supporting media includes serum-free medium supplemented with thrombopoietin, c-Kit ligand and Flt3 ligand.

Methods for Treatment

Transduction of wild-type HOX proteins promotes the proliferation of hematopoietic stem cells (HSCs), but requires frequent administration to overcome its short protein half-life (~1 hour). Conversely, the degradation-resistant, HOX(m) proteins of the instant disclosure confer a growth advantage over wild-type HOX proteins in myeloid progenitor cells. For example, direct transduction of recombinant HOXB4(m) protein to human adult HSCs significantly enhanced their maintenance in a more primitive state both in vitro and when transplanted in NOD/SCID/IL2R-γ$^{null}$ (NSG) mice when compared to transduction with wild-type HOXB4 protein. Taken together these results demonstrate that stable HOX(m) proteins of the present disclosure overcome a major technical hurdle in the expansion of adult HSCs and early progenitors for therapeutic use Bone marrow regeneration after transplant is a function of proper engraftment of transplanted cells. In certain embodiments, engraftment of transplanted cells is long term engraftment of the cells. In other embodiments, the present methods encompass improved engraftment of hematopoietic stem cells (HSCs) derived from human umbilical cord blood, peripheral blood, bone marrow, or spleen.

The term "engraftment" or "engrafting" is used in here to refer to the ability of a hematopoietic cell to implant into the bone marrow for an extended period of time, e.g., at least 3 months, at least six months, at least one year. Implantation resulting from engraftment may be detected directly, (e.g., by biopsy) or by the production of progeny cells in the blood which are labeled (i.e., GFP, YFP, RFP) or marked (i.e., $CD34^+$) to facilitate detection.

Methods for stem cell transplantation for treatment of diseases, disorders or abnormalities in humans are well known in the art. For example, see Manual of Stem Cell and Bone Marrow Transplantation (Cambridge University Press, 2009), Stem cell transplantation: biology, processing, and therapy (Wiley-VCH, 2006), and Practical Hematopoietic Stem Cell Transplantation (Wiley-Blackwell, 2007). These documents are hereby incorporated by reference.

Hematopoietic stem cell transplants are performed by employing adult HSCs mobilized into the peripheral blood following treatment with G-CSF. HSCs obtained from umbilical cord blood or adult G-CSF-mobilized bone marrow/peripheral blood have a much lower success rate in transplantation because cord blood is limited in the number of $CD34^+$ stem/progenitor cells that can be obtained (1-2× $10^6$), an amount typically insufficient for the engraftment of adults. Therefore, adults require the use of two or more cord blood units, which requires a double match and considerable increased cost. Transplantation with HSCs derived from a sibling or unrelated matched bone marrow or G-CSF-mobilized peripheral blood donors requires a minimum of $2 \times 10^6$ $CD34^+$ cells/kg. Similarly, about one-third of autologous transplant patients require additional rounds of G-CSF treatment to mobilize sufficient numbers of HSCs for transplant. The methods of the present disclosure provides an important advance in elucidating a post-translational regulatory mechanism of HOX protein stability that can now be exploited to maintain the proliferative and repopulative potential of HSCs and stem cells.

Specifically, the current disclosure demonstrates that HOX mutant proteins showed a stronger effect in expanding and engrafting G-CSF-mobilized HSCs, which can be used to eliminate the need for repeat HSC mobilization procedures.

Therefore, the current disclosure further provides a method for treatment of diseases, disorders, or abnormalities in a subject requiring a stem cell based therapy. In one non-limiting example, the method of treatment includes transplanting to a subject a therapeutically effective amount of a stem cell population prepared in accordance with the stem cell expansion methods disclosed hereinabove, for the treatment of a disease or condition in need of transplantation of stem cells.

In certain embodiments, the present methods of stem cell transplantation can be used as part of the treatment of a "subject in need of transplantation of stem cells". As used herein, the term "subject in need of transplantation of stem cells" include, e.g., subjects suffering from a disorder that can be treated by, i.e., can benefit from, transplantation of stem cells.

Transplantation of the expanded stem cell population of the present disclosure may be occur by any suitable means of administration, for example, by subcutaneous, intravenous, intramuscular, or intracisternal injection or infusion techniques (e.g., cell suspensions); in formulations containing non-toxic, acceptable vehicles or homing moieties. The expanded stem cell population of the present disclosure may, for example, be administered in a form suitable for immediate release and engraftment. Immediate release and engraftment may be achieved by the use of suitable targeting agent (i.e., linker to a cell specific antibody or surface marker) comprising the present cells.

In addition to primates, such as humans, a variety of other mammals can be treated according to the method of the present disclosure. For instance, mammals including, but not limited to, cows, sheep, goats, horses, dogs, cats, guinea pigs, rats or other bovine, ovine, equine, canine, feline, rodent or murine species can be treated. However, the methods can also be practiced in other species, such as avian species (e.g., chickens).

The subjects treated using the current methods, in which cells targeted for modulation is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the expanded stem cell population that will elicit the biological or medical response of a tissue, system, animal or human that is being sought by the researcher, veterinarian, medical doctor or other clinician. It will be understood, however, that the specific amount of expanded stem cells and frequency of administration for any particular subject may be varied and will depend upon a variety of factors including the activity of the specific cells employed, the stability of the mutant HOX proteins and, the age, body weight, general health, sex, diet, mode and time of administration, rate of engraftment, drug combination, the severity of the particular condition, and the host undergoing therapy. In a specific example, a therapeutically effective amount of expanded cells transplanted into a subject is an amount capable of engrafting such transplanted cells in the subject, whereby such cells ameliorate of the symptoms of the disorder by eliciting the desired biological response.

The terms "administration of" and or "administering a" composition should be understood to mean providing, delivering or transplanting stem cells to the subject in need of treatment. In certain embodiments, stem cells administered to a subject can be in an amount between $1 \times 10^6$ to $5 \times 10^8$ cells/kg body weight, which can be delivered in single or multiple doses. In other embodiments, stem cells provided to a subject can be in an amount of about $10^6$, $2 \times 10^6$, $5 \times 10^6$, $10^7$, $5 \times 10^7$, $10^8$ cells/kg body weight, or an amount between any of the above listed values. The cells may be administered on a regimen of 1 to 5 times per day, 1-3 times per day, once or twice per day, or every other day.

It will be understood, however, that the specific amount of cells administered to a subject and the frequency of administration may vary for a particular patient varied and may depend upon a variety of factors including the activity of the specific cells employed, the stability of the cells provided, the age, body weight, general health, sex, diet, mode and time of administration, the severity of the particular condition, and the subject undergoing therapy.

Certain types of stem cells may also be used as transplants for subjects whose bone marrow was destroyed by the high doses of chemotherapy or radiation therapy used to treat some cancers.

In one embodiment, the subject in need of transplantation of stem cells suffers from a hematopoietic and circulatory (blood cells, etc.) disease or condition, including, but not limited to, anemia (e.g., aplastic anemia (particularly, severe aplastic anemia), renal anemia, cancerous anemia, secondary anemia, refractory anemia, etc.), cancer or tumors (e.g., leukemia); and after chemotherapy therefore, hematopoietic failure, thrombocytopenia, acute myelocytic leukemia (particularly, a first remission (high risk group), a second remission and thereafter), acute lymphocytic leukemia (particularly, a first remission, a second remission and thereafter), chronic myelocytic leukemia (particularly, chronic period, transmigration period), malignant lymphoma (particularly, a first remission (high-risk group), a second remission and thereafter), multiple myeloma (particularly, an early period after the onset), and the like. The present disclosure also targets heart failure, stenocardia, cardiac infarction, arrhythmia, valvular heart diseases, myocardial/pericardial diseases, congenital heart diseases (e.g., atrial septal defect, ventricular septal defect, arterial duct patency, tetralogy of Fallot), arterial diseases (e.g., arterial sclerosis, aneurysm, etc.), venous diseases (e.g., phlebeurysm, etc.), and lymph vessel diseases (e.g., lymphatic edema), sickle cell disease, and treatment of radiation induced injuries, autoimmune diseases, cerebral palsy, critical limb ischemia, degenerative joint disease, diabetes type 2, heart failure, multiple sclerosis, osteoarthritis, rheumatoid arthritis, bone disorders (e.g., osteitis, osteoporosis, osteoarthritis, osteosarcoma), skin disorders (e.g., psoriasis, esczema, skin cancer), corneal diseases (e.g., keratoconus, keratitis) and spinal injury.

Stem cells for use in the present method of treatment may be the subject's own cells (autologous transplantation) or those of a donor (allogeneic transplantation). When the subject's own stem cells are used, they may be collected before chemotherapy or radiation therapy "in vivo collection" because these treatments may damage stem cells. They may be injected back into the body after the treatment, such as increasing or expanding ("in vivo expansion") the quality of the cells in the subject. In yet another embodiment, the subjects stem cells may be collected and stored and expanded outside of the subject (i.e., "ex vivo expansion") and injected back into the subject when necessary.

In a specific embodiment of the present disclosure, CD34+ cells obtained from a subject are provided with a HOXB4 (m) or HOXA9(m) protein, expanded in culture and transplanted into a subject in need thereof (e.g., human subject or animal subject) by intravenous injection. After transplantation, the number of CD34+ cells in the bone marrow and multi-lineage engraftment in the recipient subject can be evaluated to determine whether transplanted cells are properly engrafted into the bone marrow and functioning properly.

Current methods for stem cell storage involve collection of stem cells from embryonic cord blood and the collection of stem cells from blood donations. The utility of these techniques are limited because of the small proportion of total number of stem cells in the peripheral blood and because only a limited amount of blood may be collected from a blood transfusion. An advantage of using stem cells from an adult is that the subject's own cells can be expanded in culture using the methods described in the present invention and then reintroduced into the subject. Thus, there is also an unmet need in collecting human stem cell population for long term cryogenic storage, for example in a stem cell bank, and for the eventual thawing of the cryopreserved cell population for the treatment of a disease by autologous transfer. Preservation of stem cells for cyrostorage is well known in the art. For example, see Culture of human stem cells (Wiley-Liss, 2007), and Cryopreservation and freeze-drying protocols (Humana Press, 2007). These documents are hereby incorporated by reference.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1. General Methods

Cell Cultures, Plasmids and Protein Extracts

Steady-state levels of epitope-tagged HOX proteins in response to increasing levels of MYC-CUL4A were determined following transfection of 293T cells with 1 µg of the indicated HOX plasmids (lanes 1-4) and 1, 3, or 9 µg MYC-CUL4A (lane 2-4). All DNA amounts were normalized with vector DNA, and protein levels were detected using standard Western blotting techniques with anti-MYC (Roche), anti-HA (Covance) and anti-β-actin (Santa Cruz) antibodies.

To measure the effect of CUL4A silencing on HOXB4 half-life, HeLa cells were transiently transfected with 6 µg MYC-HOXB4 and 6 µg shCONTROL or 6 µg shCUL4A. Pulse-chase of transfected HeLa cells was performed as previously described in Zhang, Y., et al. *Embo J.* (2003); 22(22):6057-6067. The half-lives of $^{35}$S-labeled-MYC-HOXB4 and HOXB4 degron mutants were determined by immunoprecipitation and immunoblotting with anti-MYC antibody, and quantitated via phospho-imaging.

To determine the effect of CUL4A inhibition on the ubiquitination of MYC-HOXB4, 293T cells were transiently transfected with 3 µs MYC-HOXB4 (lanes 1-5), 3 µs HIS-ubiquitin (lanes 2-5), and 1, 3, or 9 µs V5-tagged dominant negative CUL4A (DN-CUL4A, lane 3-5). See Zhang, Y., et al. (2003). Transfected cells were treated with 25 µM MG132 for 4 hrs prior to harvesting. Cell lysates were precipitated with $Ni^{2+}$-NTA agarose beads (Qiagen), and immunoblotted with antibodies against MYC, V5 (Invitrogen), and β-tubulin (Sigma).

To determine the effect of the CUL4 ubiquitin ligases on endogenous HOXB4 protein levels in hematopoietic progenitor cells, bone marrow cells from wild-type and null Cul4a and Cul4b mice were isolated and progenitor cells were enriched using the EasySep™ Mouse Hematopoietic Progenitor Cell Enrichment Kit (Stemcell Technologies). Genotyping was performed as previously described in Liu, L., et al. *Cell Res.* (2012); 22(8):1258-1269. HOXB4 protein levels were analyzed by Western blot analysis using standard techniques with an anti-HOXB4 antibody (Cell Signaling).

Mutations of the HOXB4 LEXE motif were generated using the QuikChange® Multi Site-Directed Mutagenesis kit (Stratagene). The eGFP-HOXB4 homeodomain (wild-type and mutant) fusion constructs were generated by PCR amplification of wild-type and mutant HOXB4 homeodomain (HD) and ligation to pEGFP-C2 (BD Bioscience). Steady-state levels of eGFP-HOXB4 HD in response to increasing levels of MYC-CUL4A expression were determined following transfection of 293T cells with 1 µs eGFP-HOXB4 WT HD (lanes 1-4) or 1 µs eGFP-HOXB4(m) HD (lanes 5-8), together with 1 µs (lanes 2 and 6), 3 µs (lanes 3 and 7), or 9 µs (lanes 4 and 8) MYC-CUL4A. All DNA amounts were normalized with vector DNA, and protein levels were detected using standard Western blotting techniques.

Wild-type and mutant HA-HOXB4 were retrovirally transduced into 32D cells as previously described and sorted by GFP expression. See Zhang, Y., et al., (2003). The MIGRI retroviral vector alone (lacking a transgene) was also transduced into 32D cells as a negative control. Ectopic expression of wild-type and mutant HA-HOXB4 was confirmed by standard Western blotting techniques. The stable lines were cultured in IMDM (Mediatech) supplemented with 20% Serum Replacement (Invitrogen), 1% penicillin/streptomycin (Mediatech) and 2 ng/mL murine IL-3 (Miltenyi Biotech). Cells were passaged every three days, and counted daily. HOXB4 half-life was measured following addition of 50 µM cycloheximide (final concentration). Samples were harvested at the indicated times, and HA-HOXB4 levels were determined by Western blotting.

In Vitro HSC Assays

To express recombinant protein, wild-type and mutant HOXB4 were subcloned into the pTAT-HA expression vector (generous gift from Dr. Steven Dowdy). Recombinant protein was purified (see, e.g., Lu, S J., et al. *Stem Cells Dev.* (2007); 16(4):547-559), and desalted using PD-10 columns (GE Healthcare Life Sciences). G-CSF-mobilized CD34$^+$ cells were grown in serum-free QBSF medium (Quality Biological) supplemented with 100 ng/mL thrombopoietin (Miltenyi Biotech), c-Kit ligand (Amgen) and Flt3 ligand (Amgen), and 1 µg/mL recombinant protein every other day. Colony-forming cell (CFC) assays were performed with G-CSF-mobilized CD34$^+$ cells cultured in triplicate (500 cells/plate). Each plate contained 1 mL of semisolid medium with 1.2% methylcellulose (Corning Chemicals), 20% Serum Replacement, 80 µM 2-mercaptoethanol, 2 mM L-glutamine, 1% penicillin/streptomycin, 0.125 mM hemin (Sigma), 20 ng/mL G-CSF (Amgen), c-Kit ligand and IL-3 (Amgen), and 6 units/mL erythropoietin (Amgen) and 1 µg/mL recombinant proteins. Colonies were scored after two weeks of incubation at 37° C.

Limiting dilution cobblestone area-forming colony (CAFC) assays were performed in 96-well format with the indicated numbers of G-CSF-mobilized CD34$^+$ cells added to MS-5 stromal cells concurrently with transplantation into NSG mice. Cultures were changed weekly with the replacement of one-half of the culture volume with fresh media (MEM Alpha (MSKCC) supplemented with 12.5% horse serum (HyClone), 12.5% fetal calf serum, 80 µM 2-mercaptoethanol, 2 mM L-glutamine, 1% penicillin/streptomycin and 1 µM hydrocortisone (Sigma)). After 5 weeks, CAFCs were scored using an inverted-phase microscope as phase-dark hematopoietic areas of at least five cells beneath the MS-5 stromal layer.

Transplantation Experiments

NOD/SCID/IL2R-γ$^{null}$ (NSG) mice bred in the MSKCC animal facility were irradiated at 250 cGy (cesium source). Each irradiated mouse (five mice/group) was transplanted via tail vein injection with 3×10$^5$ CD34$^+$ G-CSF-mobilized adult HSCs (AllCells, LLC, Emeryville, Calif.) treated with two rounds of purified recombinant wild-type or HOXB4(m) protein (1 µg/mL) added immediately following and 24 hours after overnight cytokine stimulation (100 ng/mL thrombopoietin, c-Kit ligand and Flt3 ligand). Mice were sacrificed at twelve weeks post-transplantation, and bone marrow was harvested for FACS analysis using monoclonal antibodies against human CD19, CD33, CD34 and CD45 (Miltenyi Biotech).

Example 2. CUL4A Mediates Ubiquitination of HOXB4

In order to evaluate whether HOXB4 is subject to CUL4A-mediated degradation was first undertaken. The steady-state levels of MYC-tagged HOXB4 decreased correspondingly to increasing levels of MYC-CUL4A (FIG. 1A). Conversely, knockdown of CUL4A by shRNA prolonged the half-life of HOXB4 (FIG. 1B, 1E). Following the addition of MG132, it was observed that HOXB4 is polyubiquitinated, and enforced expression of dominant-negative CUL4A dramatically reduced ubiquitination of HOXB4 in a dose-dependent manner (FIG. 1C).

To determine the role of CUL4A and CUL4B on HOXB4 stability in hematopoietic progenitor cells, the endogenous HOXB4 protein levels in hematopoietic stem and progenitor cells derived from Cul4a- and Cul4b-null mice were compared with those from their wild-type littermates. It was observed that the deletion of either Cul4a or Cul4b resulted in the increased accumulation of HOXB4 protein levels (FIG. 1D). Taken together, these results indicate a role for both CUL4A and CUL4B as regulators of HOXB4 stability. Herein, CUL4A is utilized as representative of CUL4 E3 ligase family proteins in order to investigate the biochemical mechanisms and functional implications of the CUL4 family in orchestrating the ubiquitination and degradation of HOXB4.

Figure 2:
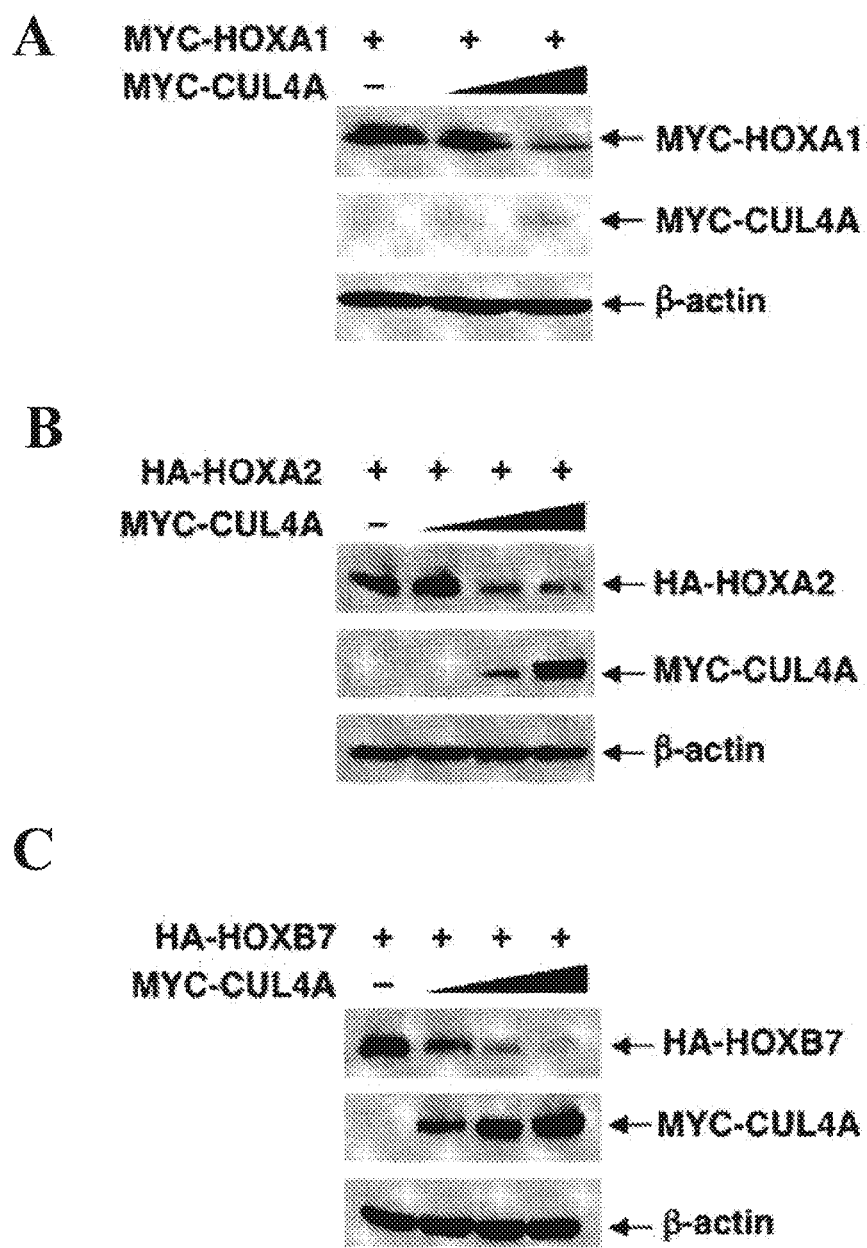
FIG. 2. CUL4A targets multiple HOX proteins for degradation. Steady-state levels of indicated HOX proteins were reduced in response to increasing levels of transfected CUL4A, as determined by immunoblotting with the appropriate antibodies. The steady-state levels of representative HOX paralogous group proteins, including A. HOXA1, B. HOXA2, C. HOXB7, D. HOXB8, E. HOXA11 and F. HOXB13 decreased corresponding to increasing levels of MYC-CUL4A transfection. β-actin levels were determined by immunoblotting as loading controls.
Figure 2:
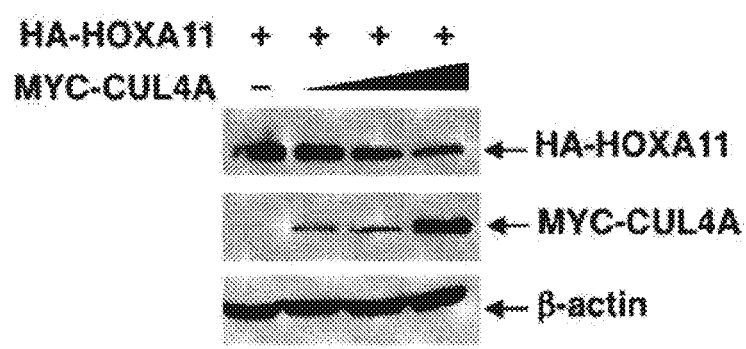
Figure 2:
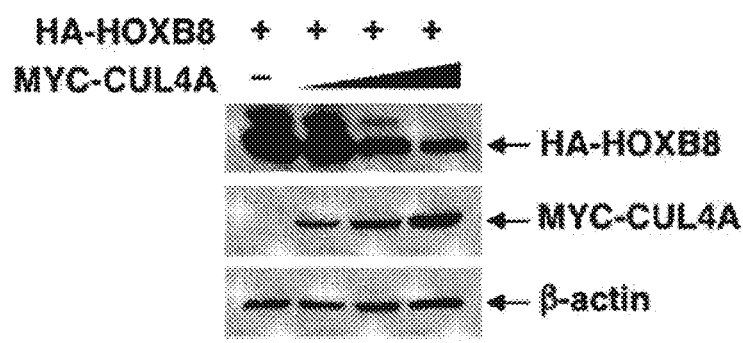
Figure 2:
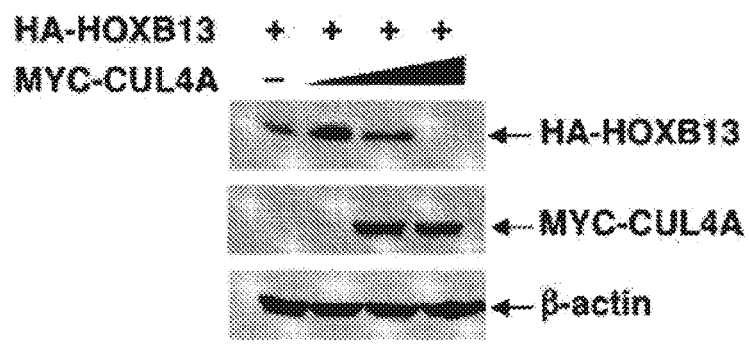

Next, a study to determine whether other HOX proteins are subject to CUL4A-mediated degradation was undertaken. Indeed, the steady-state levels of representative HOX paralogous group proteins, including HOXA1, A2, B7, B8, A11 and A13, also decreased corresponding to increasing levels of MYC-CUL4A (FIG. 2), while the HOX co-factor Meis1 was not subjected to CUL4A-mediated degradation. Therefore, the post-translational regulation of HOX protein stability by CUL4A ubiquitin ligase is mediated through a conserved mechanism, such as recognition of a common HOX protein domain.

Example 3. CUL4A-Specific HOXB4 Degron

Figure 3:
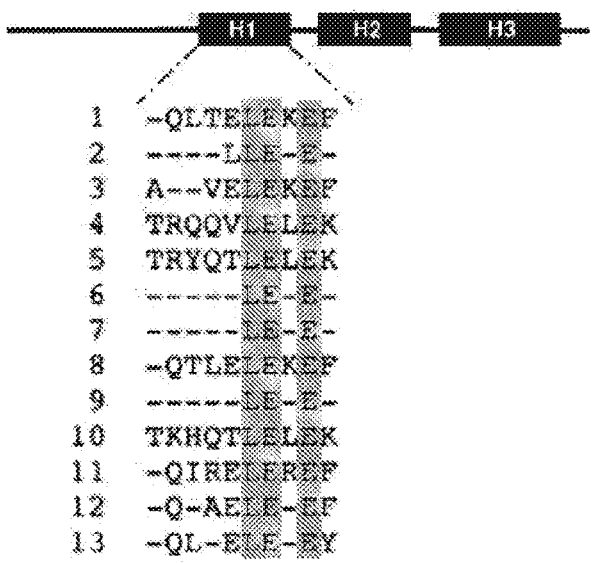
FIG. 3. HOXB4 homeodomain contains the CUL4A-dependent degron. A. Sequence alignment of the homeodomains of all HOX paralogous groups revealed a conserved LEXE motif. B, C. Half-lives of HOXB4 LEXE mutants. Pulse-chase analysis of HOXB4 LEXE mutants (M1: L175D; M2: L175D, E176K; M3: L175D, E176K, E178K) was performed following transfection of the MYC-tagged proteins into HeLa cells, $^{35}$S-Met labeling, and immunoprecipitation with the anti-MYC antibody. The percentages of HOXB4 and the LEXE mutant proteins remaining at each time point were normalized relative to time 0 of each protein. The percentages of HOXB4 or LEXE mutant proteins remaining at each time point are indicated. D. Determination of the steady-state levels of GFP-HOXB4 homeodomain fusion protein in response to increasing MYC-CUL4A levels by immunoblotting with antibodies against GFP or MYC epitope tags or β-actin as loading control.
Figure 3:
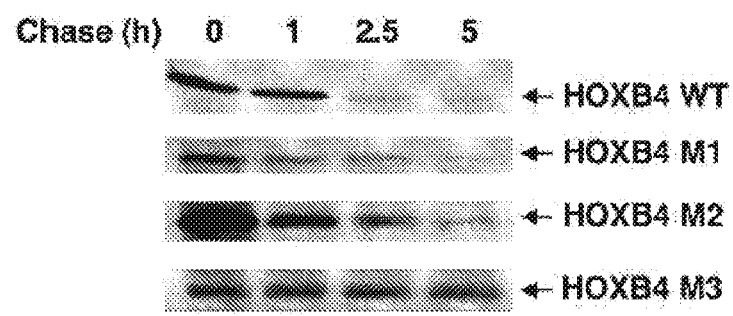
Figure 3:
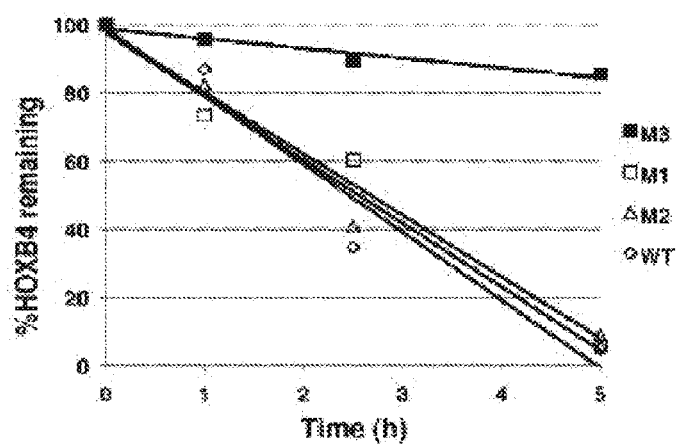
Figure 3:
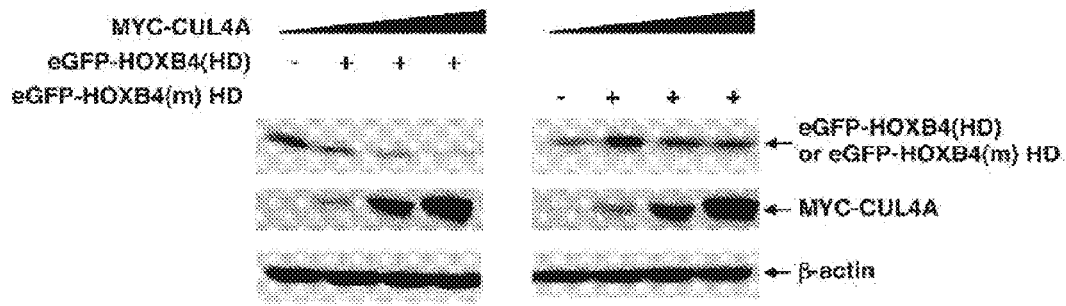

A sequence alignment of the highly conserved homeodomain present in all HOX proteins revealed a conserved LEXE motif in helix I of the full-length protein that is not involved in DNA binding (FIG. 3A). Because several HOX paralogous groups are post-translationally regulated by CUL4A, it was examined whether the conserved LEXE motif may comprise the CUL4A-dependent degron, or the substrate sequence that directs its recognition by a specific ubiquitin ligase for degradation. While mutation of the first two residues of the LEXE [SEQ. ID NO: 2] motif prolonged the HOXB4 protein half-life compared to wild-type protein, the triple mutant, HOXB4(M3) [SEQ. ID No.:4], dramatically extended HOXB4 protein stability (FIG. 3B, C).

To determine if the LEXE motif in the context of its native tertiary structure is required to target proteins for CUL4A-mediated degradation, wild-type or mutant HOXB4 homeodomain was fused to eGFP, a long-lived protein that is not a native CUL4A substrate. The fusion of eGFP to the wild-type HOXB4 homeodomain conferred sensitivity to CUL4A-mediated degradation, while the eGFP-HOXB4 mutant homeodomain protein remained resistant to increasing levels of CUL4A (FIG. 3D). These studies show that the LEXE motif within helix I of the HOXB4 homeodomain constitutes a transferable signal that is both necessary and sufficient to mediate CUL4A-dependent degradation.

Example 4. HOX(m) Proteins Enhances 32D Proliferation

Figure 4:
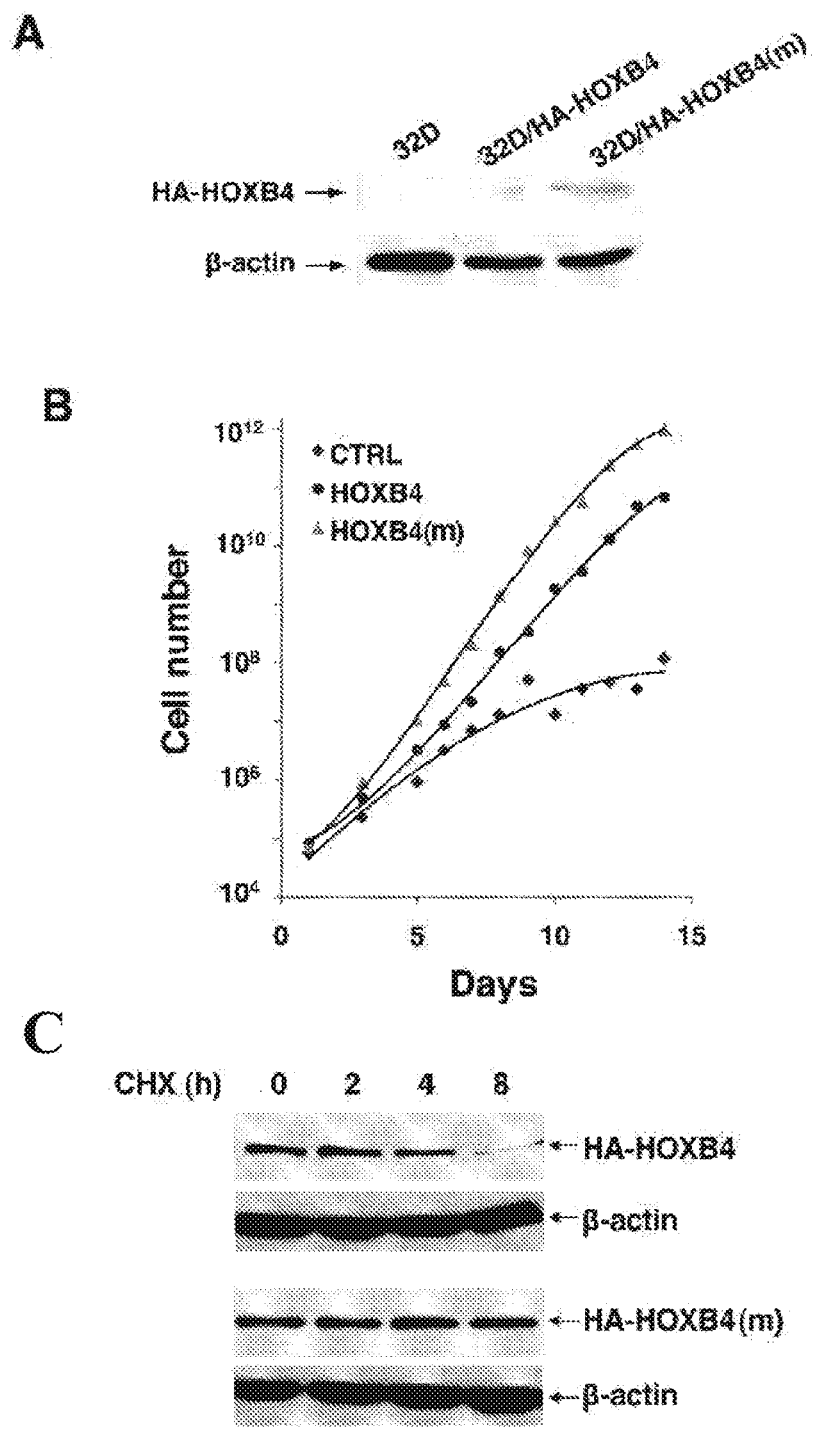
FIG. 4. Degradation-resistant HOXB4 confers proliferative advantage to 32D myeloid cell line. A. Expression levels of HA-HOXB4 (wild-type or mutant) in 32D stable lines, as determined by immunoblotting with the anti-HA antibody. B. Cumulative expansion of 32D stable lines in serum-free medium. C. Cycloheximide chase analysis for the half-lives of HA-HOXB4 (wild-type or mutant) in 32D stable lines. HA-HOXB4 or HA-HOXB4(m) levels were determined by immunoblotting at the indicated time points. β-actin levels were determined as loading control. D. HOXB4 and HOXB4(m) mRNA expression levels were determined by quantitative PCR (qPCR) in 32D cells stably expressing the indicated transgenes in comparison of those infected with the control MIGRI retrovirus. Data were normalized against b-actin expression in the same cell line. Data for each sample were run in triplicate. Error bars are indicated in each column.
Figure 4:
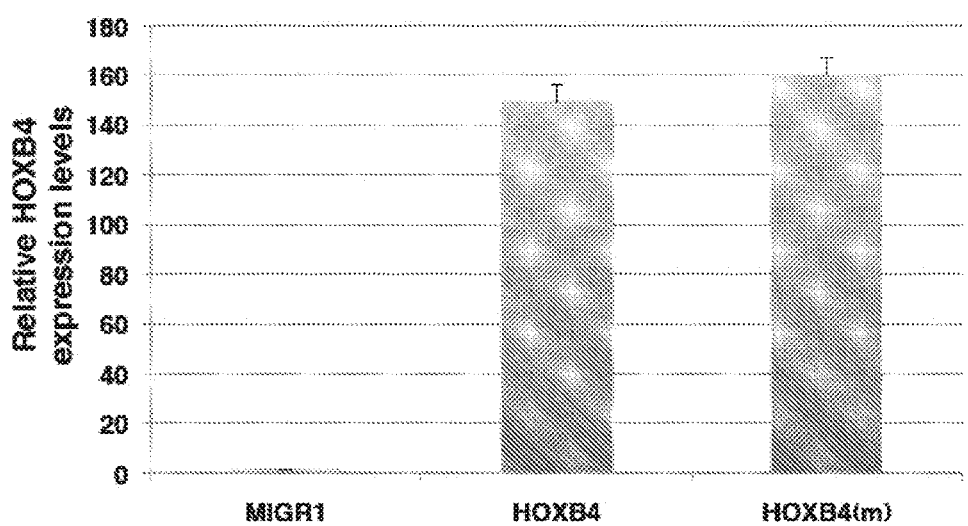

To determine whether HOXB4 degradation by CUL4A impacts the proliferation potential of hematopoietic cells, HOXB4 or HOXB4(m) was retrovirally transduced into the 32D murine myeloid progenitor cell line and steady-state levels of HOXB4(m) were observed to be higher than wild-type HOXB4, while the mRNA levels were comparable (FIG. 4A, 4D). Next, a comparison of their growth in serum-free medium and showed that ectopic expression of either wild-type or degradation-resistant HOXB4 resulted in a distinct growth advantage over control cells. Remarkably, 32D cells expressing HOXB4(m) showed a further 10-fold increase in cell number compared to wild-type HOXB4-transduced cells after 15 days in culture, representing a 10,000-fold increase compared to 32D cells transduced with vector alone (FIG. 4B). Correspondingly, the half-life of HOXB4(m) was substantially longer than wild-type HOXB4 (FIG. 4C), indicating that the enhanced protein stability of HOXB4(m) contributes to the growth advantage of 32D myeloid progenitors.

Example 5. HOX(m) Proteins Maintain HSC Potential

HSCs derived from peripheral blood are more readily available and abundant than those derived from umbilical cord blood (UCB) for stem cell transplantation. To determine the effect of HOXB4 on postnatal HSC expansion, the expression of HOXB4 in CD34+ cells from cord blood was first compared with that in G-CSF-mobilized adult peripheral blood. As determined by quantitative RT-qPCR in FIG. 5A, HOXB4 mRNA levels are 12-fold lower in G-CSF-mobilized adult CD34+ cells than UCB CD34+ cells, suggesting that HOXB4 may be a limiting factor in the ex vivo expansion of G-CSF-mobilized adult HSCs, and that ectopic introduction of HOXB4 protein into G-CSF-mobilized adult CD34+ cells may promote more dramatic HSC expansion than UCB CD34+ cells.

Figure 5:
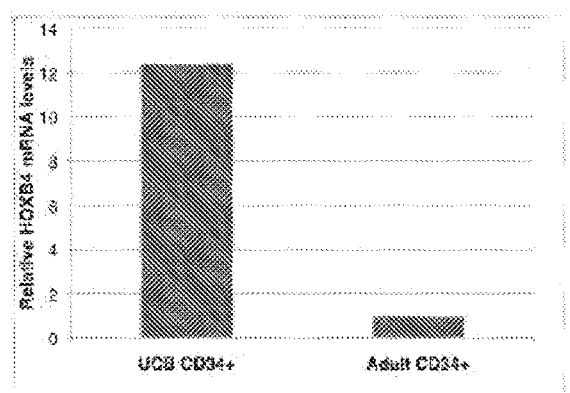
FIG. 5. Direct transduction of recombinant degradation-resistant HOXB4 protein maintains G-CSF-mobilized CD34+ cells in a more primitive state than wild-type HOXB4. A. Comparison of HOXB4 mRNA expression levels in CD34+ UCB cells vs. CD34+G-CSF-mobilized cells. B, C. Comparison of granulocyte-monocyte (CFU-GM) and erythroid (BFU-E, CFU-E) colony-forming cells following addition of wild-type or degradation-resistant recombinant HOXB4 protein to CD34+G-CSF-mobilized cells. D. Limiting dilution CAFC assays of G-CSF-mobilized CD34+ cells following addition of wild-type or degradation-resistant HOXB4 protein. E. Multi-lineage engraftment of G-CSF-mobilized CD34+ cells treated with wild-type or degradation-resistant recombinant HOXB4 protein in NSG mice (n=8 per group) 12 weeks post-primary transplantation. The experiment was independently repeated three times.
Figure 5:
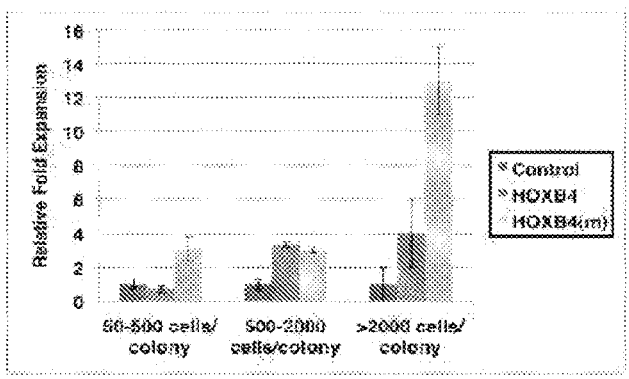
Figure 5:
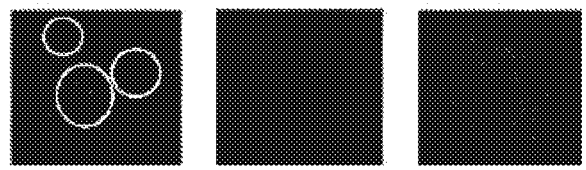
Figure 5:
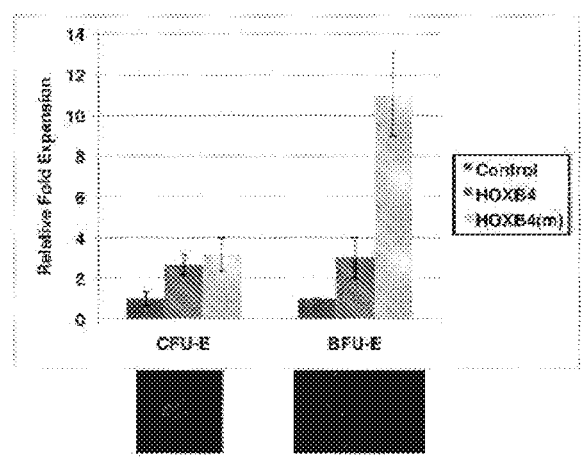
Figure 5:
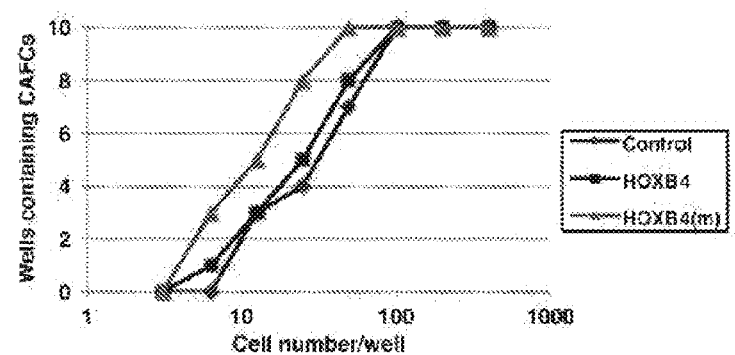
Figure 5:
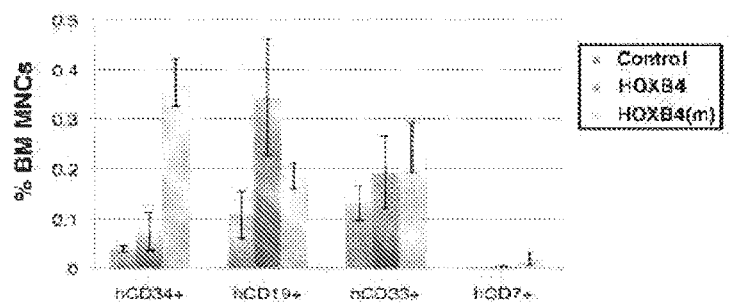
Figure 6:
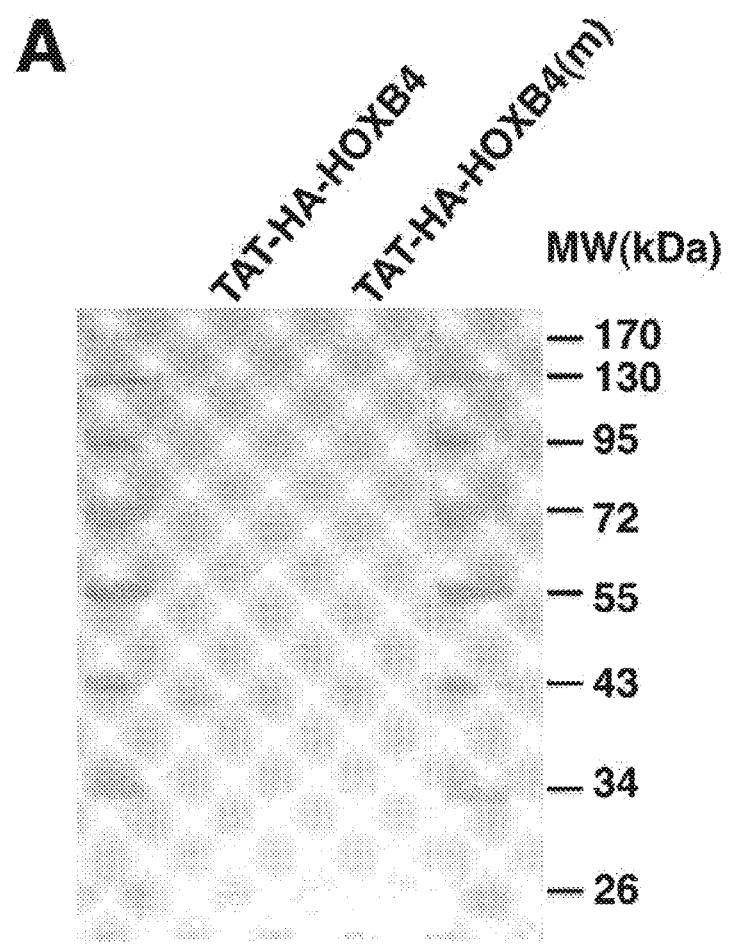
FIG. 6. Localization of recombinant TAT-HA-HOXB4 and TAT-HA-HOXB4(m) proteins in G-CSF-mobilized CD34+ cells. A. Coomassie-stained gel of purified recombinant TAT-HA-HOXB4 and TAT-HAHOXB4(m). Approximately 1 μg of each recombinant protein was loading onto a 9% SDS-PAGE gel. We consistently observed that the TAT-HA-HOXB4(m) recombinant protein ran slightly higher than the TAT-HA-HOXB4 protein. However, we completely sequenced both constructs and did not observe any additional unintended mutations in TAT-HA-HOXB4 (m). B. To determine the intracellular localization of recombinant HOXB4 protein, 1 μg of wild-type or degradation-resistant HOXB4 protein was incubated with 1×105 G-CSF mobilized CD34+ cells in QBSF-60 medium for 30 minutes, then fixed with 2% paraformaldehyde for 10 minutes on ice. Fixed cells were cytospun onto glass slides at 400 rpm for 5 minutes, then fixed again with 100% ethanol for 10 minutes. Samples were blocked with PBS+0.1% Triton X-100, 1% BSA and 5% goat serum for 30 minutes at room temperature. HA.11 monoclonal antibody was diluted 1:50 in blocking buffer and incubated with samples for 1 hour at room temperature. Alexa Fluor 488 goat anti-mouse secondary antibody was diluted 1:500 in blocking buffer and incubated with samples for 30 minutes at room temperature. Cells were counterstained with DAPI, and coverslips were mounted with FluorSave reagent prior to visualization by fluorescence microscopy.
Figure 6:
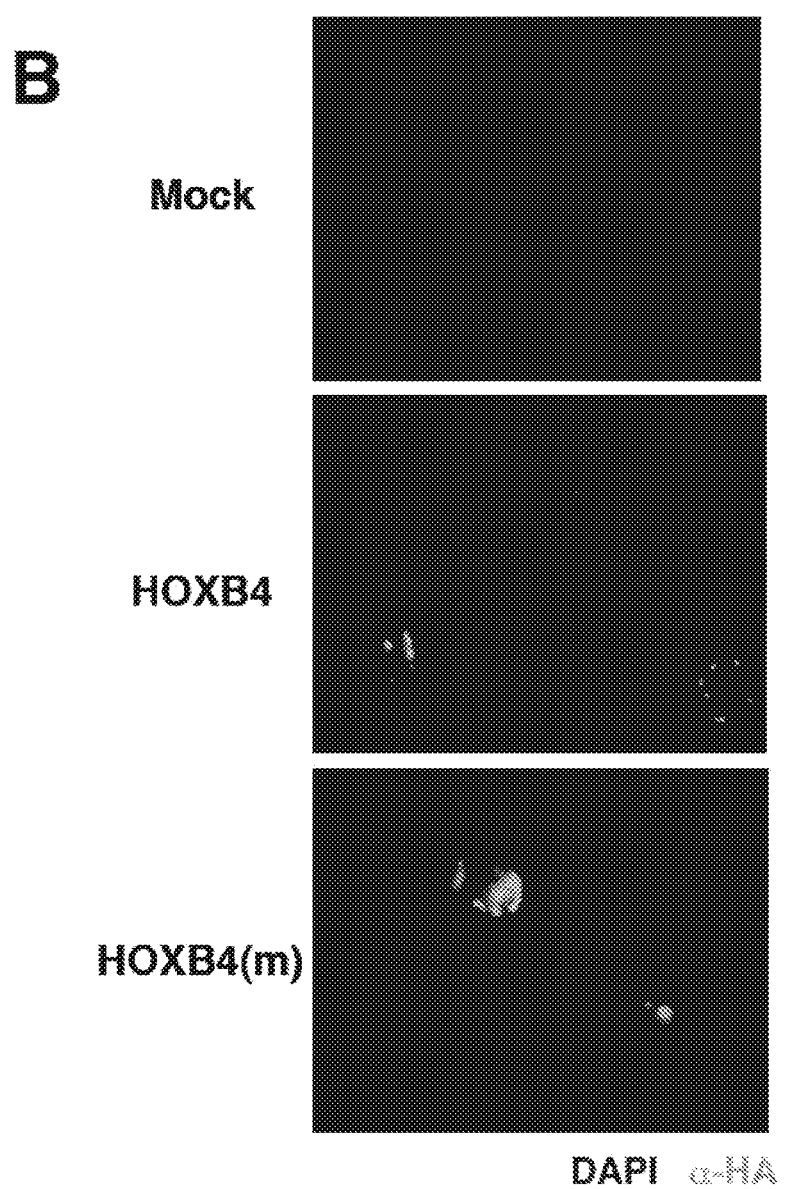
Figure 7:
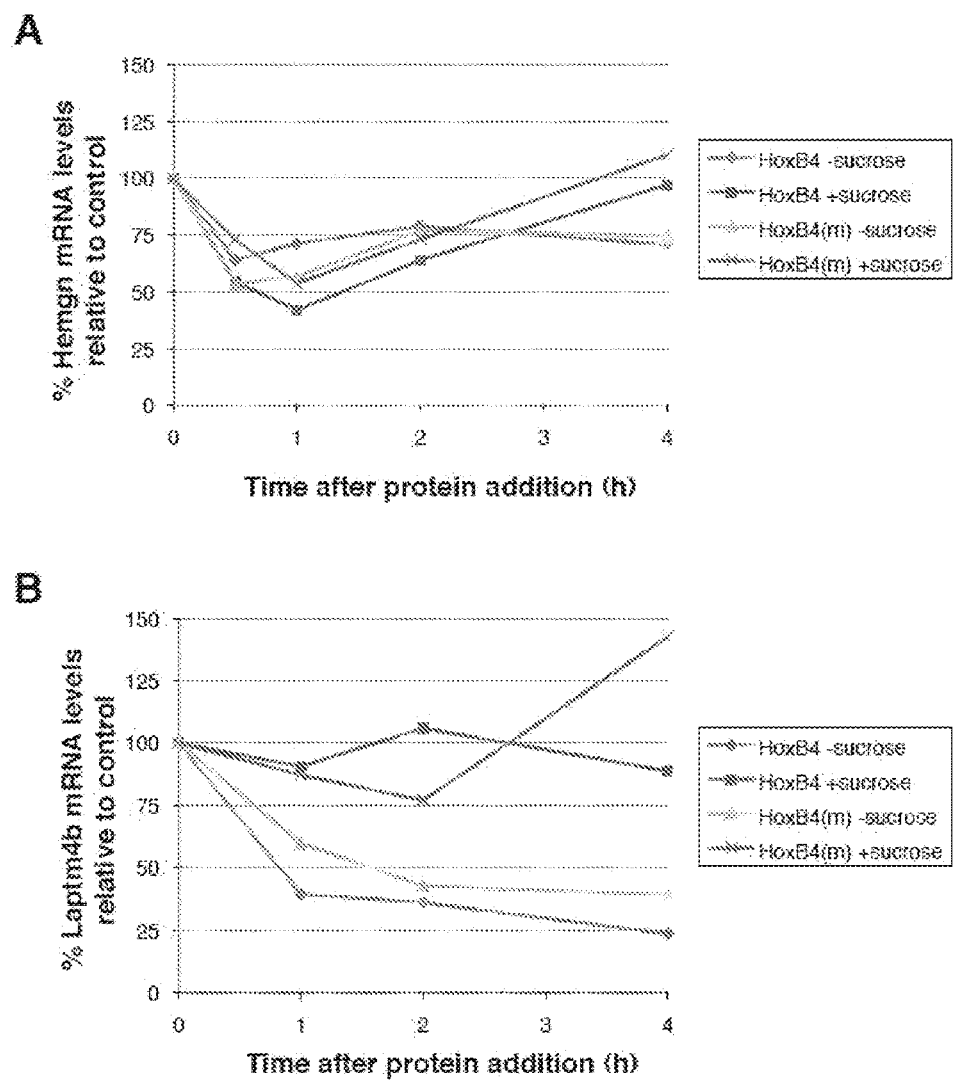
FIG. 7. Quantitative RT-PCR of identified HOXB4 transcriptional targets in KG1 cells following the addition of recombinant wild-type or degradation-resistant HOXB4 protein. Recombinant HOXB4 protein was added to 5×105 KG1 cells at the indicated amounts, and harvested at the indicated times. Sucrose was added with the recombinant protein to a final concentration of 250 mM as noted. RNA was extracted using TRIzol Reagent, and cDNA was synthesized for real-time quantitative PCR of HOXB4 transcriptional targets.
Figure 8:
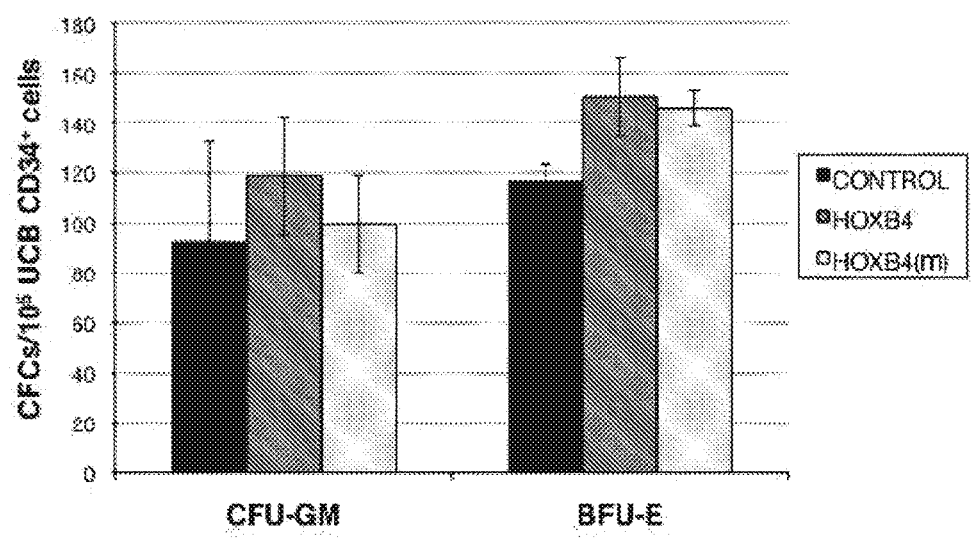
FIG. 8. Umbilical cord blood CD34+ cells responded similarly to recombinant TAT-HA-HOXB4 and TAT-HA-HOXB4(m) in the colony-forming cell assay. Purified recombinant TAT-HOXB4 or TAT-HOXB4(m) were administered onto UCB34+ cells and the number of CFU-GM or BFU-E were counted.
Figure 9:
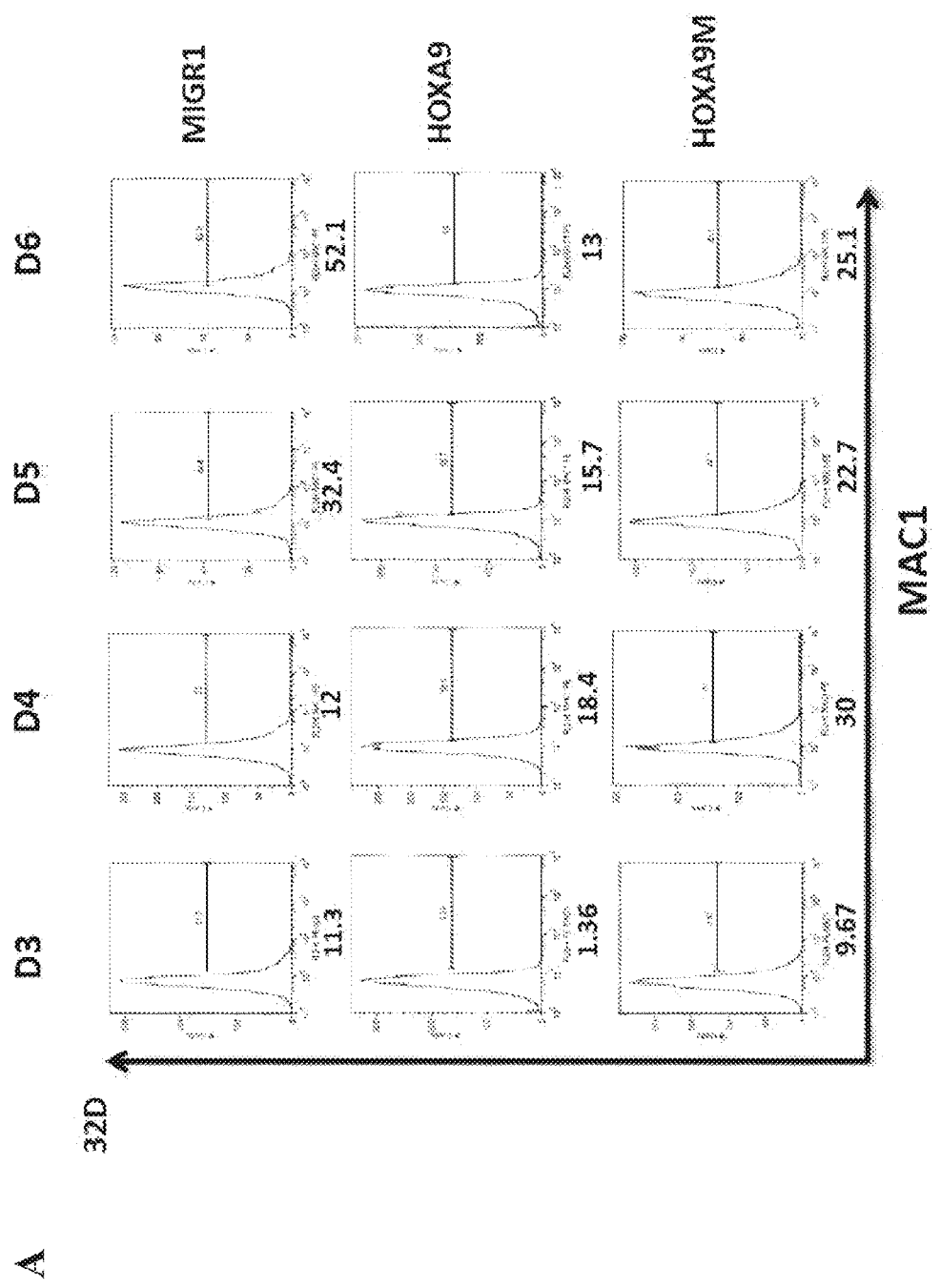
FIG. 9. HOXA9(m) protein maintains HSC potential and promotes proliferation without increasing HSC differentiation. A. FACS sorting of immortalized myeloid progenitor cells (32D cells) expressing MIGR1 retroviral vector alone (control), wild-type HOXA9 protein alone or recombinant HOXA9(m) protein alone reveals that when purified recombinant HOXA9(m) protein is expressed in HSCs differentiation over the course of 6 days (D3-D6) is reduced dramatically when compared to 32D cells expressing wild-type HOXA9 protein. The numbers indicated below each FACS data point indicate the % of cells exhibiting macrophage markers (i.e., differentiated cells). B. Colony forming assays. Comparison of granulocyte-monocyte (CFU-GM), granulocyte-erythroid-marcrophage-monocyte (CFU-GEMM), and erythroid (BFU-E, CFU-E) colony-forming cells following addition of wild-type HOXA9 or recombinant HOXA9(m) protein to CD34+G-CSF-mobilized 32D cells, indicates that cells expressing HOXA9(m) protein do not change the primitive nature of the cells, and thus can expand cells without directly and terminally differentiating HSCs.
Figure 9:
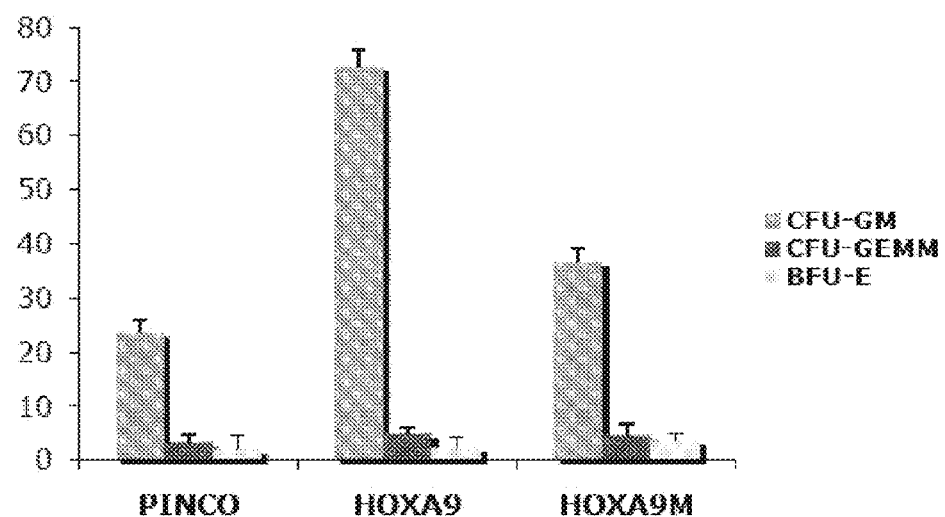

One goal of engineering a degradation-resistant HOXB4 (m) protein is to overcome the labile nature of HOXB4 ($t_{1/2}$~1 hour) used in protein-based ex vivo expansion of HSC and progenitor cells. To elucidate the stability of HOXB4(m) proteins, HOXB4 and HOXB4(m) were tagged with the cell-penetrating HIV TAT protein transduction domain that allows efficient translocation across cellular membranes. TAT-HA-HOXB4 and TAT-HA-HOXB4(m) were expressed as hexahistine-tagged fusions in E. coli, affinity-purified, and applied to G-CSF-mobilized adult CD34+ cells for evaluation in clonogenic assays. Cell entry and peri-nuclear localization of recombinant HOXB4 and HOXB4(m) protein were observed in G-CSF-mobilized CD34+ cells (FIG. 6B), consistent with the typical punctate distribution of transduced TAT-fusion proteins. Diffused nuclear localization was also observed, especially for TAT-HA-HOXB4(m) (FIG. 6B). The transcriptional activity of putative HOXB4 target genes (e.g., Hemgn, Laptm4b) were similar following the addition of wild-type or degradation-resistant HOXB4 protein (FIG. 7). As shown in FIG. 5B-C, the total number of both myeloid and erythroid colony-forming cells increased >10-fold with the addition of HOXB4(m) compared to wild-type HOXB4 protein. Moreover, myeloid (CFU-GM) and erythroid burst-forming cells (BFU-E) grown in the presence of HOXB4(m) were significantly larger and more frequent (FIG. 5B-C) In contrast, UCB CD34+ cells responded similarly following the addition of recombinant wild-type or degradation-resistant HOXB4 protein (FIG. 8) further highlighting the effect of HOXB4(m) in G-CSF-mobilized adult HSCs.

Limiting dilution cobblestone area-forming colony (CAFC) assays were also performed to quantify the number of HSCs in G-CSF-mobilized adult CD34+ cells that were treated with either wild-type or degradation-resistant HOXB4 recombinant protein. Untreated cells served as the baseline control. Addition of degradation-resistant HOXB4 (m) protein doubled the number of HSCs measured by limiting dilution compared to both control and G-CSF-mobilized CD34+ cells treated with wild-type HOXB4 protein (FIG. 5D), indicating that the prolonged half-life of HOXB4 recombinant protein increased the efficiency in maintaining and expanding G-CSF-mobilized HSCs ex vivo.

Example 6. Transplantation of Stem Cell Populations Treated with HOX Mutant Proteins To determine the effect of wild-type versus degradation-resistant HOXB4 protein on the engraftment of G-CSF-mobilized adult HSCs and progenitors, CD34+ cells were treated with recombinant protein, transplanted into sub-lethally irradiated NOD/SCID/IL2R-$\gamma^{null}$ (NSG) mice, and analyzed 10 weeks post-transplantation. HOXB4(m) protein significantly enhanced the number of human CD34+ cells in the bone marrow of primary transplanted mice compared to both control and wild-type HOXB4 protein-treated mice, and multi-lineage engraftment was also observed (FIG. 5E). Strikingly, a 5-fold increase in the percentage of primitive CD34+ HSCs and progenitors was detected in the engrafted bone marrow of HOXB4(m)-transduced NSG mice. Thus, the degradation-resistant HOXB4(m) protein enhances proliferation of G-CSF-mobilized HSCs in vitro and maintains the primitive state of HSCs more effectively than wild-type HOXB4 in vivo.

Example 7. Development of a Practical Method of Delivering HOXB4 Had Yet to be Devised that Ensures Safety and Pharmaceutical Compatibility Although the ectopic expression of HOXB4 following retroviral transduction was not reported to induce leukemia in mice, follow-up studies have since identified a causal relationship between the development of leukemia in large mammals and their transplantation with HSCs constitutively expressing HOXB4. Moreover, direct transduction of wild-type HOXB4 protein recapitulated the expansion of HSCs similar to enforced expression of the HOXB4 gene, but required frequent replenishing of the recombinant protein due to the short protein half-life.

Here, it has been determined that CUL4A is responsible for the proteasome-mediated degradation of multiple HOX proteins. Furthermore, the current disclosure has identified a conserved homeodomain motif as a significant determinant for CUL4A-directed activity. For example, fusion of the HOXB4 homeodomain to a non-native CUL4A substrate was sufficient to target the protein for CUL4A-mediated degradation, indicating that the HOXB4 homeodomain contains a bona fide CUL4A degron (FIG. 3D).

The present disclosure also shows that the deletion of either CUL4 family members led to increased accumulation of HOXB4, indicating a redundant role for CUL4A and CUL4B in vivo. Moreover, degradation-resistant HOXB4 enhanced the proliferation of the murine myeloid progenitor 32D cell line and the generation of more primitive myeloid and erythroid colonies by G-CSF CD34+ progenitor cells compared to wild-type HOXB4, further revealing that the effect of degradation-resistant HOXB4 can be augmented in hematopoietic progenitor cells with limiting levels of HOXB4.

Example 8. HOXA9(m) Protein Expression Maintains HSC Potential and Promotes the Expansion of Myeloid Progenitor Cells Mouse bone marrow cells were isolated from HOXA9−/− mice, and infected with retrovirus expressing control virus (e.g., PINCO, MIGR1), wild-type HOXA9 protein or HOXA9(m) protein and cells were sorted and induced with G-CSF. FACS analyses were used to determine cell differentiation at various time points over the course of several days. The results show that when transduced into 32D myeloid progenitor cells, HOXA9(m) protein inhibited myeloid differentiation.

Cells were cultured in myeloid progenitor immortalization condition, and cells were counted and plated every 2 days. Cells expressing wild-type HOXA9 protein or HOXA9(m) protein were then compared and counted to determine the amount of cells grown. Furthermore, colony formation assays (CFU) were conducted to evaluate the effect of wild-type HOXA9 protein and HOXA9(m) protein on lineage-specific progenitor cells. Taken together, HOXA9(m) protein expression promoted proliferation of myeloid progenitor cells without terminally differentiation. Therefore, HOXA9(m) proteins of the present disclosure are capable of expansion of HSCs.

---

What is claimed is:

1. An isolated HOX mutant protein, wherein said HOX mutant protein differs from the wild-type HOX protein by having a mutation in the LEXE motif set forth in SEQ ID NO: 2.

2. The isolated protein of claim 1, wherein said HOX mutant protein is a HOXB4 mutant protein, wherein said HOXB4 mutant protein differs from the wild-type HOXB4 protein of SEQ ID NO: 1 in amino acids 175, 176 and 178.

3. The isolated protein of claim 2, wherein the differences in said amino acids comprise a substitution of Leu175 in the wild-type HOXB4 protein to a charged amino acid in the HOXB4 mutant protein.

4. The isolated protein of claim 2, wherein the differences in said amino acids comprise substitution of Glu176 and Glu178 to a positively charged amino acid.

5. The isolated protein of claim 4, wherein said positively charged amino acid is Lysine.

6. The isolated protein of claim 2, wherein said HOXB4 mutant protein comprises the amino acid sequence set forth in SEQ ID NO: 3 or SEQ ID NO: 4.

7. The isolated protein of claim 1, wherein said HOX mutant protein is a HOXA9 mutant protein, wherein said HOXA9 mutant protein differs from the wild-type HOXA9 protein of SEQ ID NO: 5 in amino acids 219, 220, and 222.

8. The isolated protein of claim 7, wherein the differences in said amino acids comprise a substitution of L219 in the wild-type HOXA9 protein to a charged amino acid in the HOXA9 mutant protein.

9. The isolated protein of claim 7, wherein the differences in said amino acids comprise substitution of Glu220 and Glu222 to a positively charged amino acid.

10. The isolated protein of claim 9, wherein said positively charged amino acid is Lysine.

11. The isolated protein of claim 7, wherein said HOXA9 mutant protein comprises the amino acid sequence set forth in SEQ ID NO: 7.

12. A method for expanding a stem cell population in culture, comprising providing to the stem cell population in culture a HOX mutant protein in an amount effective to expand the stem cell population, wherein said HOX mutant protein differs from the wild-type HOX protein by having a mutation in the LEXE motif set forth in SEQ ID NO: 2.

13. The method of claim 12, wherein the stem cell population is an adult stem cell population.

14. The method of claim 12, wherein the stem cell population is a hematopoietic stem cell population.

15. The method of claim 14, wherein the hematopoietic stem cell population is obtained from umbilical cord blood, peripheral blood, bone marrow, or spleen.

16. The method of claim 12, wherein the HOX mutant protein is a HOXB4 mutant protein, wherein said HOXB4 mutant protein is provided to the stem cell population by administration to the culture media.

17. The method of claim 16, wherein the HOXB4 mutant protein is attached to a transport moiety that transports the HOXB4 mutant protein into the stem cells.

18. The method of claim 17, wherein the transport moiety is an HIV-1 transactivator of transcription (TAT) peptide, a herpes-simplex virus-1 (HSV) DNA binding protein VP22, the Mtb carrier domain from *Mycobacterium tuberculosis* Mce1 protein or a *Drosophila* Antennapedia (Antp) homeotic transcription factor protein transduction domain.

19. The method of claim 12, wherein the HOX mutant protein is provided introducing a vector comprising a polynucleotide encoding the HOX mutant protein to the stem cell population.

20. The method of claim 19, wherein said vector is a viral vector.

21. The method of claim 20, wherein said viral vector is selected from the group consisting of an AAV vector and a retroviral vector.

22. The method of claim 12, wherein the HOX mutant protein is selected from the group consisting of a protein comprising SEQ ID NO: 3, a protein comprising SEQ ID NO: 4, a protein comprising SEQ ID NO: 6, and a protein comprising SEQ ID NO: 7.

23. The method of claim 22, wherein said HOX mutant protein is a HOXB4 mutant protein comprising the amino acid sequence set forth in SEQ ID NO: 3 or SEQ ID NO: 4.

24. The method of claim 22, wherein said HOX mutant protein is a HOXA9 mutant protein comprising the amino acid sequence set forth in SEQ ID NO: 6 or SEQ ID NO: 7.

25. The method of claim 12, further comprising culturing said stem cell population in media comprising FMS-like tyrosine kinase-3 (FLT-3) ligand, Thrombopoietin (TPO), and/or CD117 (c-Kit) ligand.

26. A method for treating a subject in need of transplantation of stem cells, comprising transplanting a therapeutically effective amount of a stem cell population prepared in accordance with the method of claim 12.

27. The method of claim 26, wherein said subject in need of transplantation of stem cells suffers from a blood disorder, leukemia, lymphoma or anemia.

* * * * *

SEQUENCE LISTING

```
<160> NUMBER OF SEQ ID NOS: 7

<210> SEQ ID NO 1
<211> LENGTH: 251
<212> TYPE: PRT
<213> ORGANISM: Homo sapiens

<400> SEQUENCE: 1

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro Gly Tyr Tyr Ala Gly Gly Gln Arg Arg Glu Ser Ser Phe
        35                  40                  45

Gln Pro Glu Ala Gly Phe Gly Arg Arg Ala Ala Cys Thr Val Gln Arg
    50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
            85                  90                  95

Pro Pro Ala Gly Ala Leu Leu Pro Glu Pro Gly Gln Arg Cys Glu Ala
            100                 105                 110

Val Ser Ser Ser Pro Pro Pro Pro Cys Ala Gln Asn Pro Leu His
            115                 120                 125

Pro Ser Pro Ser His Ser Ala Cys Lys Glu Pro Val Val Tyr Pro Trp
130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
            165                 170                 175

Leu Glu Lys Glu Phe His Tyr Asn Arg Tyr Leu Thr Arg Arg Arg Arg
            180                 185                 190

Val Glu Ile Ala His Ala Leu Cys Leu Ser Glu Arg Gln Ile Lys Ile
            195                 200                 205

Trp Phe Gln Asn Arg Arg Met Lys Trp Lys Lys Asp His Lys Leu Pro
            210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
                245                 250

<210> SEQ ID NO 2
<211> LENGTH: 4
<212> TYPE: PRT
```

```
<213> ORGANISM: Artificial Sequence
<220> FEATURE:
<223> OTHER INFORMATION: human wild-type HOX LEXE motif within the first
      alpha helical domain of the HOXB4 homeodomain region
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Glu Xaa Glu
1

<210> SEQ ID NO 3
<211> LENGTH: 251
<212> TYPE: PRT
<213> ORGANISM: Artificial Sequence
<220> FEATURE:
<223> OTHER INFORMATION: mutant human HOXB4 protein sequence, including
      an amino acid substitution at position 175, 176 and 178
<220> FEATURE:
<221> NAME/KEY: MISC_FEATURE
<222> LOCATION: (175)..(175)
<223> OTHER INFORMATION: Xaa: G, P, A, V, I, M, C, F, Y, W, H, K, R, Q,
      N, E, D, S or T
<220> FEATURE:
<221> NAME/KEY: MISC_FEATURE
<222> LOCATION: (176)..(176)
<223> OTHER INFORMATION: Xaa: G, P, A, V, I, M, C, F, Y, W, H, K, R, Q,
      N, D, L, S or T
<220> FEATURE:
<221> NAME/KEY: MISC_FEATURE
<222> LOCATION: (178)..(178)
<223> OTHER INFORMATION: Xaa: G, P, A, V, I, M, C, F, Y, W, H, K, R, Q,
      N, D, L, S or T

<400> SEQUENCE: 3

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro Gly Tyr Tyr Ala Gly Gly Gln Arg Arg Glu Ser Ser Phe
        35                  40                  45

Gln Pro Glu Ala Gly Phe Gly Arg Arg Ala Ala Cys Thr Val Gln Arg
    50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
            85                  90                  95

Pro Pro Ala Gly Ala Leu Leu Pro Glu Pro Gly Gln Arg Cys Glu Ala
            100                 105                 110

Val Ser Ser Ser Pro Pro Pro Pro Cys Ala Gln Asn Pro Leu His
        115                 120                 125

Pro Ser Pro Ser His Ser Ala Cys Lys Glu Pro Val Val Tyr Pro Trp
    130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Xaa Xaa
                165                 170                 175

Leu Xaa Lys Glu Phe His Tyr Asn Arg Tyr Leu Thr Arg Arg Arg Arg
            180                 185                 190

Val Glu Ile Ala His Ala Leu Cys Leu Ser Glu Arg Gln Ile Lys Ile
        195                 200                 205
```

```
Trp Phe Gln Asn Arg Arg Met Lys Trp Lys Asp His Lys Leu Pro
            210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
            245                 250

<210> SEQ ID NO 4
<211> LENGTH: 251
<212> TYPE: PRT
<213> ORGANISM: Artificial Sequence
<220> FEATURE:
<223> OTHER INFORMATION: mutant human HOXB4 protein sequence,
      including L175D, E176K and E178K amino acid substitutions

<400> SEQUENCE: 4

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro Gly Tyr Tyr Ala Gly Gly Gln Arg Arg Glu Ser Ser Phe
        35                  40                  45

Gln Pro Glu Ala Gly Phe Gly Arg Arg Ala Ala Cys Thr Val Gln Arg
    50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
            85                  90                  95

Pro Pro Ala Gly Ala Leu Leu Pro Glu Pro Gly Gln Arg Cys Glu Ala
            100                 105                 110

Val Ser Ser Ser Pro Pro Pro Pro Cys Ala Gln Asn Pro Leu His
            115                 120                 125

Pro Ser Pro Ser His Ser Ala Cys Lys Glu Pro Val Val Tyr Pro Trp
            130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Asp Lys
            165                 170                 175

Leu Lys Lys Glu Phe His Tyr Asn Arg Tyr Leu Thr Arg Arg Arg Arg
            180                 185                 190

Val Glu Ile Ala His Ala Leu Cys Leu Ser Glu Arg Gln Ile Lys Ile
            195                 200                 205

Trp Phe Gln Asn Arg Arg Met Lys Trp Lys Asp His Lys Leu Pro
            210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
            245                 250

<210> SEQ ID NO 5
<211> LENGTH: 272
<212> TYPE: PRT
<213> ORGANISM: Homo sapiens

<400> SEQUENCE: 5

Met Ala Thr Thr Gly Ala Leu Gly Asn Tyr Tyr Val Asp Ser Phe Leu
1               5                   10                  15
```

Leu Gly Ala Asp Ala Ala Asp Glu Leu Ser Val Gly Arg Tyr Ala Pro
            20                  25                  30

Gly Thr Leu Gly Gln Pro Pro Arg Gln Ala Ala Thr Leu Ala Glu His
        35                  40                  45

Pro Asp Phe Ser Pro Cys Ser Phe Gln Ser Lys Ala Thr Val Phe Gly
50                  55                  60

Ala Ser Trp Asn Pro Val His Ala Ala Gly Ala Asn Ala Val Pro Ala
65                  70                  75                  80

Ala Val Tyr His His His His His His Pro Tyr Val His Pro Gln Ala
                85                  90                  95

Pro Val Ala Ala Ala Ala Pro Asp Gly Arg Tyr Met Arg Ser Trp Leu
            100                 105                 110

Glu Pro Thr Pro Gly Ala Leu Ser Phe Ala Gly Leu Pro Ser Ser Arg
        115                 120                 125

Pro Tyr Gly Ile Lys Pro Glu Pro Leu Ser Ala Arg Arg Gly Asp Cys
    130                 135                 140

Pro Thr Leu Asp Thr His Thr Leu Ser Leu Thr Asp Tyr Ala Cys Gly
145                 150                 155                 160

Ser Pro Pro Val Asp Arg Glu Lys Gln Pro Ser Glu Gly Ala Phe Ser
                165                 170                 175

Glu Asn Asn Ala Glu Asn Glu Ser Gly Gly Asp Lys Pro Pro Ile Asp
            180                 185                 190

Pro Asn Asn Pro Ala Ala Asn Trp Leu His Ala Arg Ser Thr Arg Lys
        195                 200                 205

Lys Arg Cys Pro Tyr Thr Lys His Gln Thr Leu Glu Leu Glu Lys Glu
    210                 215                 220

Phe Leu Phe Asn Met Tyr Leu Thr Arg Asp Arg Arg Tyr Glu Val Ala
225                 230                 235                 240

Arg Leu Leu Asn Leu Thr Glu Arg Gln Val Lys Ile Trp Phe Gln Asn
                245                 250                 255

Arg Arg Met Lys Met Lys Lys Ile Asn Lys Asp Arg Ala Lys Asp Glu
            260                 265                 270

<210> SEQ ID NO 6
<211> LENGTH: 272
<212> TYPE: PRT
<213> ORGANISM: Artificial Sequence
<220> FEATURE:
<223> OTHER INFORMATION: mutant HOXA9 protein sequence, including an
      amino acid substitution at position 219, 220, or 222
<220> FEATURE:
<221> NAME/KEY: MISC_FEATURE
<222> LOCATION: (219)..(219)
<223> OTHER INFORMATION: Xaa: G, P, A, V, I, M, C, F, Y, W, H, K, R,
      Q, N, E, D, S or T
<220> FEATURE:
<221> NAME/KEY: MISC_FEATURE
<222> LOCATION: (220)..(220)
<223> OTHER INFORMATION: Xaa: G, P, A, V, I, M, C, F, Y, W, H, K, R, Q,
      N, E, D, S or T
<220> FEATURE:
<221> NAME/KEY: MISC_FEATURE
<222> LOCATION: (222)..(222)
<223> OTHER INFORMATION: Xaa: G, P, A, V, I, M, C, F, Y, W, H, K, R, Q,
      N, D, L, S or T

<400> SEQUENCE: 6

Met Ala Thr Thr Gly Ala Leu Gly Asn Tyr Tyr Val Asp Ser Phe Leu
1               5                   10                  15

Leu Gly Ala Asp Ala Ala Asp Glu Leu Ser Val Gly Arg Tyr Ala Pro
            20                  25                  30

Gly Thr Leu Gly Gln Pro Pro Arg Gln Ala Ala Thr Leu Ala Glu His
            35                  40                  45

Pro Asp Phe Ser Pro Cys Ser Phe Gln Ser Lys Ala Thr Val Phe Gly
        50                  55                  60

Ala Ser Trp Asn Pro Val His Ala Ala Gly Ala Asn Ala Val Pro Ala
65                  70                  75                  80

Ala Val Tyr His His His His His Pro Tyr Val His Pro Gln Ala
            85                  90                  95

Pro Val Ala Ala Ala Ala Pro Asp Gly Arg Tyr Met Arg Ser Trp Leu
            100                 105                 110

Glu Pro Thr Pro Gly Ala Leu Ser Phe Ala Gly Leu Pro Ser Ser Arg
            115                 120                 125

Pro Tyr Gly Ile Lys Pro Glu Pro Leu Ser Ala Arg Arg Gly Asp Cys
            130                 135                 140

Pro Thr Leu Asp Thr His Thr Leu Ser Leu Thr Asp Tyr Ala Cys Gly
145                 150                 155                 160

Ser Pro Pro Val Asp Arg Glu Lys Gln Pro Ser Glu Gly Ala Phe Ser
                165                 170                 175

Glu Asn Asn Ala Glu Asn Glu Ser Gly Gly Asp Lys Pro Pro Ile Asp
            180                 185                 190

Pro Asn Asn Pro Ala Ala Asn Trp Leu His Ala Arg Ser Thr Arg Lys
            195                 200                 205

Lys Arg Cys Pro Tyr Thr Lys His Gln Thr Xaa Xaa Leu Xaa Lys Glu
            210                 215                 220

Phe Leu Phe Asn Met Tyr Leu Thr Arg Asp Arg Tyr Glu Val Ala
225                 230                 235                 240

Arg Leu Leu Asn Leu Thr Glu Arg Gln Val Lys Ile Trp Phe Gln Asn
            245                 250                 255

Arg Arg Met Lys Met Lys Lys Ile Asn Lys Asp Arg Ala Lys Asp Glu
            260                 265                 270

<210> SEQ ID NO 7
<211> LENGTH: 272
<212> TYPE: PRT
<213> ORGANISM: Artificial Sequence
<220> FEATURE:
<223> OTHER INFORMATION: mutant human HOXA9 protein sequence, including
      amino acid substitutions L219D, E220K and E222K

<400> SEQUENCE: 7

Met Ala Thr Thr Gly Ala Leu Gly Asn Tyr Tyr Val Asp Ser Phe Leu
1               5                   10                  15

Leu Gly Ala Asp Ala Ala Asp Glu Leu Ser Val Gly Arg Tyr Ala Pro
            20                  25                  30

Gly Thr Leu Gly Gln Pro Pro Arg Gln Ala Ala Thr Leu Ala Glu His
            35                  40                  45

Pro Asp Phe Ser Pro Cys Ser Phe Gln Ser Lys Ala Thr Val Phe Gly
        50                  55                  60

Ala Ser Trp Asn Pro Val His Ala Ala Gly Ala Asn Ala Val Pro Ala
65                  70                  75                  80

Ala Val Tyr His His His His His Pro Tyr Val His Pro Gln Ala
            85                  90                  95

Pro Val Ala Ala Ala Ala Pro Asp Gly Arg Tyr Met Arg Ser Trp Leu
            100                 105                 110

Glu Pro Thr Pro Gly Ala Leu Ser Phe Ala Gly Leu Pro Ser Ser Arg

|  | 115 |  |  |  | 120 |  |  |  | 125 |  |  |  |
|---|---|---|---|---|---|---|---|---|---|---|---|---|
| Pro | Tyr | Gly | Ile | Lys | Pro | Glu | Pro | Leu | Ser | Ala | Arg | Arg | Gly | Asp | Cys |
|  | 130 |  |  |  | 135 |  |  |  | 140 |  |  |  |
| Pro | Thr | Leu | Asp | Thr | His | Thr | Leu | Ser | Leu | Thr | Asp | Tyr | Ala | Cys | Gly |
| 145 |  |  |  |  | 150 |  |  |  | 155 |  |  |  | 160 |
| Ser | Pro | Pro | Val | Asp | Arg | Glu | Lys | Gln | Pro | Ser | Glu | Gly | Ala | Phe | Ser |
|  |  |  | 165 |  |  |  |  | 170 |  |  |  |  | 175 |
| Glu | Asn | Asn | Ala | Glu | Asn | Glu | Ser | Gly | Gly | Asp | Lys | Pro | Pro | Ile | Asp |
|  |  | 180 |  |  |  |  | 185 |  |  |  |  | 190 |
| Pro | Asn | Asn | Pro | Ala | Ala | Asn | Trp | Leu | His | Ala | Arg | Ser | Thr | Arg | Lys |
|  | 195 |  |  |  |  | 200 |  |  |  |  | 205 |  |  |
| Lys | Arg | Cys | Pro | Tyr | Thr | Lys | His | Gln | Thr | Asp | Lys | Leu | Lys | Lys | Glu |
|  | 210 |  |  |  |  | 215 |  |  |  | 220 |  |  |  |
| Phe | Leu | Phe | Asn | Met | Tyr | Leu | Thr | Arg | Asp | Arg | Arg | Tyr | Glu | Val | Ala |
| 225 |  |  |  |  | 230 |  |  |  | 235 |  |  |  |  | 240 |
| Arg | Leu | Leu | Asn | Leu | Thr | Glu | Arg | Gln | Val | Lys | Ile | Trp | Phe | Gln | Asn |
|  |  |  |  | 245 |  |  |  |  | 250 |  |  |  |  | 255 |
| Arg | Arg | Met | Lys | Met | Lys | Lys | Ile | Asn | Lys | Asp | Arg | Ala | Lys | Asp | Glu |
|  |  |  | 260 |  |  |  |  | 265 |  |  |  |  | 270 |